United States Patent [19]

Spry

[11] 4,001,226

[45] Jan. 4, 1977

[54] 3-(SUBSTITUTED)CARBONYLAMINO CEPHEM DERIVATIVES

[75] Inventor: Douglas O. Spry, Indianapolis, Ind.

[73] Assignee: Eli Lilly and Company, Indianapolis, Ind.

[22] Filed: Dec. 4, 1974

[21] Appl. No.: 529,676

[52] U.S. Cl. .......................... 260/243 C; 424/246
[51] Int. Cl.² ............. C07D 501/20; C07D 501/60
[58] Field of Search ................................ 260/243 C

[56] References Cited

FOREIGN PATENTS OR APPLICATIONS

71/3229    5/1971    South Africa ................ 260/243 C

Primary Examiner—Donald G. Daus
Assistant Examiner—Mary C. Vaughn
Attorney, Agent, or Firm—Steven R. Lammert; Walter E. Butting; Everet F. Smith

[57] ABSTRACT

7-Acylamino and 7-amino-3-(substituted)carbonylamino-3(or 2)-cephem-4-carboxylic acids and esters thereof, which are useful as antibiotics or as intermediates in preparing antibiotic substances respectively, are prepared from 7-acylamino-3-azidocarbonyl-2(or 3)-cephem-4-carboxylic acid esters via the corresponding thermally derived 3-isocyanatocephem derivatives.

30 Claims, No Drawings

3-(SUBSTITUTED)CARBONYLAMINO CEPHEM DERIVATIVES

BACKGROUND OF THE INVENTION

This invention relates to the cephalosporin class of antibiotics. In particular, this invention relates to certain of such cephalosporins having in the 3-position a carbonylamino (isocyanato) or a substituted carbonylamino group. Such groups include acylamino, ureido or substituted ureido, alkoxycarbonylamino, (alkylthio) carbonylamido, and other like groups which can be prepared by the reaction of a 3-cyanato cephem compound with an appropriate nucleophilic reagent. The compounds of this invention are therapeutically useful antibiotic compounds or intermediates useful in the preparation of such antibiotics.

Numerous antibiotics of the cephalosporin class having a variety of substituents at the 3-position have been described.

Exemplary of C-3 substituents on known cephem compounds are hydroxymethyl, alkylthiomethyl, heteroarylthiomethyl, methoxymethyl (U.S. Pat. No. 3,665,003), bromomethyl (U.S. Pat. Nos. 3,647,788, 3,668,203 and 3,637,678), formyl (U.S. Pat. No. 3,351,596, and carboxy (copending U.S. application Ser. No. 426,459).

It is an object of this invention to provide novel cephalosporin compounds which are useful as antibiotics or as intermediates in processes for preparing antibiotics.

It is another and more specific object of this invention to provide new structurally unique compounds of the cephalosporin class, wherein an isocyanate group, or a derivative thereof, is attached directly to the carbon in the 3-position of the dihydrothiazine ring.

SUMMARY OF THE INVENTION

This invention is directed to cephalosporin compounds having an isocyanate group, or a first order derivative thereof, at the 3-position of the cephem ring system. The 7-acylamino-3-isocyanatocephem compounds provided by this invention are preferably prepared by the thermal rearrangement of acylazides derived from the corresponding 7-acylamino-3-carboxy-2(or 3)-cephem-4-carboxylic acid esters. The 3-isocyanatocephem compounds are then isolated or reacted in situ with the appropriate nucleophilic reagents to provide the 7-acylamino-3-(substituted)carbonylamino-3(or 2)-cephem-4-carboxylic acid esters of the present invention. Thus, for example, the reaction of the 3-isocyanatocephem derivatives with alcohols, thiols, primary or secondary amines, or carbanionic compounds (e.g., Grignard reagents or alkyl lithium compounds) provides cephems of the present invention having as substituents at the C-3 position alkoxycarbonylamino (urethane or carbamate), (alkylthio)carbonylamino (thiocarbamate), ureido or substituted ureido, or acylamino respectively. Removal of the carboxylic acid ester protecting group gives the novel active antibiotic substances provided by this invention which compounds can be employed to combat infections caused by gram-positive and gram-negative microorganisms.

DETAILED DESCRIPTION OF THE INVENTION

The cephalosporin compounds of this invention are represented by the following Formula I:

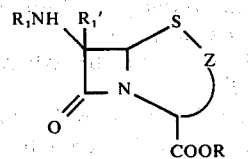

wherein Z is a group of the formula

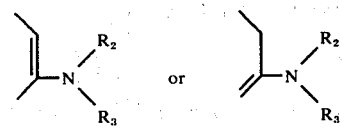

wherein $R_2$ and $R_3$ are each hydrogen or taken together form the group $=C=O$ or
wherein $R_2$ taken singly is hydrogen and $R_3$ taken singly is a. a group of the formula

wherein $R_4$ is $C_1-C_6$ alkyl, $C_3-C_6$ alkenyl, $C_1-C_6$ haloalkyl, 2,2,2-trihaloethyl, methoxybenzyl, nitrobenzyl, benzyl or phenyl; or b. a group of the formula

wherein $R_5$ is $C_1-C_6$ alkyl, phenyl, or benzyl; or c. a group of the formula

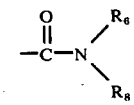

wherein $R_6$ is hydrogen, $C_1-C_6$ alkyl, benzyl, phenyl, or tolyl, and $R_8$ is hydrogen, $C_1-C_6$ alkyl, or benzyl; or wherein $R_6$ and $R_8$ and the nitrogen atom to which they are bonded taken together form a 5 or 6 membered heterocyclic ring; or d. a group of the formula

wherein $R_7$ is $C_1-C_6$ alkyl, di($C_1-C_3$alkoxycarbonyl) methyl, benzyl, or phenyl; and
wherein R is hydrogen or a carboxylic acid protecting ester forming group; $R_1'$ is hydrogen or methoxy; and $R_1$ is hydrogen or an acyl group of the formula

wherein R' is a. $C_1$-$C_7$ alkyl, $C_3$-$C_7$ alkenyl, cyanomethyl, halomethyl, 4-amino-4-carboxybutyl, 4-protected amino-4-protected carboxybutyl; or
b. $C_1$-$C_6$ alkoxy, benzyloxy, 4-nitrobenzyloxy, or 4-methoxybenzyloxy; or
c. the group —R″ wherein R″ is 1,4-cyclohexadienyl, phenyl, or substituted phenyl wherein the substituents are 1–3 halogens, hydroxy, nitro, cyano, trifluoromethyl, $C_1$-$C_4$ alkyl, $C_1$-$C_4$ alkoxy, carboxy, carboxymethyl, hydroxymethyl, aminomethyl or protected aminomethyl; or
d. an arylalkyl group of the formula

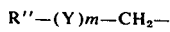

wherein R″ is as defined above, Y is O or S, and $m$ is O or 1; or
e. a substituted arylalkyl group of the formula

wherein R‴ is R″ as defined above, 2-thienyl, or 3-thienyl; W is hydroxy or protected hydroxy, carboxy or protected carboxy, amino or protected amino; or
f. a heteroarylmethyl group of the formula

wherein R⁗ is 2-thienyl, 3-thienyl, 2-furyl, 3-furyl, 2-thiazolyl, 5-tetrazolyl or 1-tetrazolyl;
and when R is hydrogen, the pharmaceutically acceptable nontoxic salts of the acids represented thereby; with the limitations that when $R_3$ is

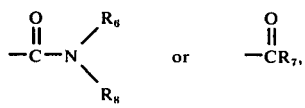

Z can only be

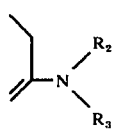

;
and when the group

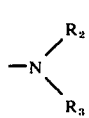

is —N=C=O, neither R nor $R_1$ can be hydrogen.

The terms employed in the foregoing definition of the compounds of the present invention have the following meanings when employed herein: The term "$C_1$-$C_6$ alkyl" refers to methyl, ethyl, n-propyl, n-butyl, isobutyl, pentyl, n-hexyl, cyclohexyl, and like aliphatic hydrocarbon chains. "$C_3$-$C_7$ alkenyl" has reference to the unsaturated hydrocarbon chains such as propenyl (allyl), butenyl, pentenyl, hexenyl, heptenyl, and the like.

"Halomethyl" refers to chloromethyl, bromomethyl, or iodomethyl. The term "$C_2$-$C_6$ haloalkyl" as employed in the above definition has reference to 2-bromoethyl, 2-chloroethyl, 2-bromopropyl, 2-iodopropyl, 2-chlorobutyl, 2-bromo-2-methylpropyl, 2-bromobutyl, 2-bromo-2-methylbutyl and like groups.

Illustrative of the group —$SR_5$ as defined above are methylthio, ethylthio, n-propylthio, isopropylthio, tertbutylthio, n-pentylthio, cyclohexylthio, n-hexylthio, phenylthio, benzylthio, and like groups.

Included within the above definition of the group —$OR_4$ as defined above are methoxy, ethoxy, n-propoxy, isopropoxy, isobutoxy, cyclohexyloxy, 2-methylbutoxy, 2-bromoethoxy, n-butoxy, 2-chloroethoxy, 3-bromobutoxy, 2-chloropropoxy, 2,2,2-trichloroethoxy, 4-methoxybenzyloxy, benzyloxy, 4-nitrobenzyloxy, phenoxy, and like groups.

Representative of the group

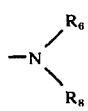

as defined above are amino, methylamino, ethylamino, dimethylamino, diethylamino, isopropylamino, butylamino, cyclohexylamino, benzylamino, methylphenylamino, phenylamino (anilino), morpholino, piperidino, pyrrolidino and like groups.

When in the above definition R″ represents a substituted phenyl group, R″ can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or dihydroxyphenyl group such as 4-hydroxyphenyl, 3-hydroxyphenyl, 2,4-dihydroxyphenyl and the like; a mononitrophenyl group such as 3- or 4-nitrophenyl; a cyanophenyl group, for example, 4-cyanophenyl; a mono or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono or disubstituted lower alkylphenyl ether for example, 2,6-dimethoxyphenyl, 4-methoxyphenyl, 3-ethoxyphenyl, 4-isopropoxyphenyl, 4-t-butoxyphenyl, 3-ethoxy-4-methoxyphenyl and the like. Also, R″ represents disubstituted phenyl groups wherein the substituents can be different for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

The term, "protected amino" as employed in the above definition has reference to an amino group substituted with one of the commonly employed amino blocking groups such as the t-butoxycarbonyl group (t-BOC); the benzyloxycarbonyl group, the 4-methoxybenzyloxycarbonyl group, the 4-nitrobenzyloxycarbonyl group, the 2,2,2-trichloroethoxycarbonyl group, the 1-carbomethoxy-2-propenyl group formed with methyl acetoacetate, the trimethylsilyl group, and like amino protecting groups. The nature of such amino protecting groups is not critical so long as the protected amino functionality is stable under the reaction conditions described hereinafter.

The term "protected hydroxy" has reference to the readily cleavable groups formed with an hydroxyl group such as the formyloxy group, the chloroacetoxy group, the benzhydryloxy group, the trityloxy group, the p-nitrobenzyloxy group, the trimethylsilyl group, and the like.

The term "protected carboxy" has reference to a carboxy group which has been protected by one of the commonly used carboxylic acid protecting ester groups employed to block or protect the carboxylic acid functionality while reactions involving other functional sites of the compound are carried out. Such protected carboxy groups are noted for their ease of cleavage by hydrolytic or by hydrogenolytic methods to the corresponding carboxylic acid. Examples of carboxylic acid protecting groups include tert-butyl, benzyl, 4-methoxybenzyl, dimethylallyl, $C_2-C_6$ alkanoyloxymethyl, β-iodoethyl, 4-nitrobenzyl, diphenylmethyl(benzhydryl), phenacyl, p-halophenacyl, 2,2,2-trichloroethyl and like ester forming moieties. The nature of such ester forming groups is not critical so long as the ester formed therewith is stable under the reaction conditions described hereinafter. Preferred carboxylic acid protecting groups are benzhydryl, 4-methoxybenzyl, dimethylallyl, and tert-butyl.

In the foregoing definitions, hydroxy, amino, and carboxy protecting groups are not exhaustively defined. The function of such groups is to protect the reactive functional groups during the preparation of the desired products and then be removed without disrupting the remainder of the molecule. Many such protecting groups are well known in the art and the use of other groups equally applicable to the process and compounds of the present invention, such as those described in J. F. W. McOmie, "Protective Groups in Organic Chemistry", Plenum Press, 1973, will be recognized as suitable. Thus, there is no novelty or inventiveness asserted with regard to the "protecting groups" alluded to in this specification.

Illustrative of the acyl groups,

as defined above are acetyl, propionyl, butyryl, hexanoyl, heptanoyl, 2-pentenoyl, acryloyl, 5-aminoadipoyl, chloroacetyl, bromoacetyl and the like.

Representative of the acyl groups

are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, 3-aminobenzoyl, 4-nitrobenzoyl and the like.

Illustrative of the acyl groups

when R' is a group of the formula R''—(Y)m—CH₂— and m is 0, are cyclohexa-1,4-diene-1-acetyl, phenylacetyl, 4-chlorophenylacetyl, 3-hydroxyphenylacetyl, 3-cyanophenylacetyl, 4-hydroxy-3-methylphenylacetyl, 4-bromophenylacetyl, 4-ethoxyphenylacetyl, 4-nitrophenylacetyl, 3,4-dimethoxyphenylacetyl and the like; and when m is 1 and Y is O, representative acyl groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenoxyacetyl, 3,4-dimethylphenoxyacetyl, 4-isopropylphenoxyacetyl, 3-cyanophenoxyacetyl, 3-nitrophenoxyacetyl and like substituted phenoxyacetyl groups; and when m is 1 and Y is S, representative phenylthioacetyl groups are phenylthioacetyl, 2,5-dichlorophenylthioacetyl, 3-chloro-4-fluorophenylthioacetyl, 4-cyanophenylthioacetyl, 3-bromophenylthioacetyl, and like acyl groups.

Illustrative of the acyl groups when R' is a substituted arylalkyl group of the formula

are the hydroxy substituted arylalkyl groups such as the 2-hydroxy-2-phenylacetyl group of the formula

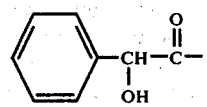

or the 2-formyloxy-2-phenylacetyl group of the formula

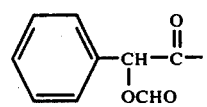

and similar groups wherein the phenyl ring is substituted, for example, 2-hydroxy-2-(4-methoxyphenyl)acetyl, 2-hydroxy-2-(3-chloro-4-hydroxyphenyl)acetyl, 2-formyloxy-2-(4-hydroxyphenyl)-acetyl, 2-hydroxy-2-(3-bromophenyl)acetyl, 2-formyloxy-2-(3,5-dichloro-4-hydroxyphenyl)acetyl, 2-formyloxy-2-(3-chloro-4-methoxyphenyl)acetyl, 2-hydroxy-2-(3-chlorophenyl)acetyl and like groups.

Representative of the acyl groups when R' is a carboxy or alkoxycarbonyl substituted arylalkyl group are 2-carboxy-2-phenylacetyl, 2-tert-butoxycarbonyl-2-phenylacetyl, 2-benzyloxycarbonyl-2-(4-chlorophenyl)acetyl, 2-carboxy-2-(4-methoxyphenyl)acetyl, 2-carboxy-2-(3-nitrophenyl)acetyl, and like groups.

When R' is an amino substituted arylalkyl group or a derivative thereof, acyl groups represented thereby include 2-amino-2-phenylacetyl, 2-amino-2-(1,4-cyclohexadien-1-yl)-acetyl, 2-tert-butoxycarbonylamino-2-phenylacetyl, 2-amino-2-(4-hydroxyphenyl)acetyl, and like acyl groups.

Representative of the acyl group

when R' is a heteroarylmethyl group of the formula R''''—CH₂— are 2-thienylacetyl, 3-thienylacetyl, 2-furylacetyl, a 2-thiazolylacetyl group of the formula

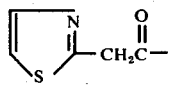

a 1-tetrazolylacetyl group of the formula

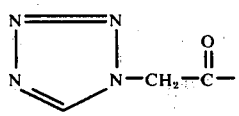

or a 5-tetrazolylacetyl group of the formula

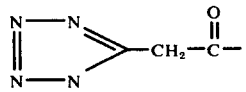

The compounds of the present invention are derived generally from 7-acylamino-3-azidocarbonyl-2(or 3)-cephem-4-carboxylic acid esters. The following reaction sequence is exemplary of the preparation of the 3-isocyanatocephems and the derivatives thereof of the present invention from a 3-azidocarbonyl-3-cephem compound:

an acylazide to an isocyanate, commonly known as a Curtius rearrangement, is a general reaction of acylazides and has been applied to acyl azide derivatives of many carboxylic acids including aliphatic, alicyclic, heterocyclic, unsaturated and those containing many functional groups.

The cephem isocyanate thereby produced is either isolated or reacted in situ with nucleophilic reagents to yield the 7-acylamino-3-(substituted)carbonylamino-3-cephem-4-carboxylic acid esters of this invention. Removal of the C-4 carboxylic acid ester protecting group and other protecting groups that may be present on the 7-substituent provides the biologicaly active 3-(substituted)carbonylaminocephem compounds of the present invention.

7-Amino-3-(substituted)carbonylamino-3-cephem-4-carboxylic acids and esters of this invention are prepared from the corresponding 7-acylamino compounds by standard PCl₅ cleavage procedures or from the corresponding 7-alkyl(or arylalkyl)oxycarbonylamino compounds by hydrogenolysis or acid hydrolysis. The method preferred for the preparation of particular 7-amino cephem compounds of this invention is dependent upon the nature of the C-3 substituent of such compound. 7-Amino-3-acylamino-3-cephem-4-carboxylic acids and esters thereof are preferably prepared by acid hydrolysis or hydrogenolysis of a corresponding 7-alkyl(or arylalkyl)oxycarbonylamino cephem derivative, whereas the 7-amino cephem compounds of this invention substituted at the C-3 position with, for example, an alkoxycarbonylamino, a ureido,

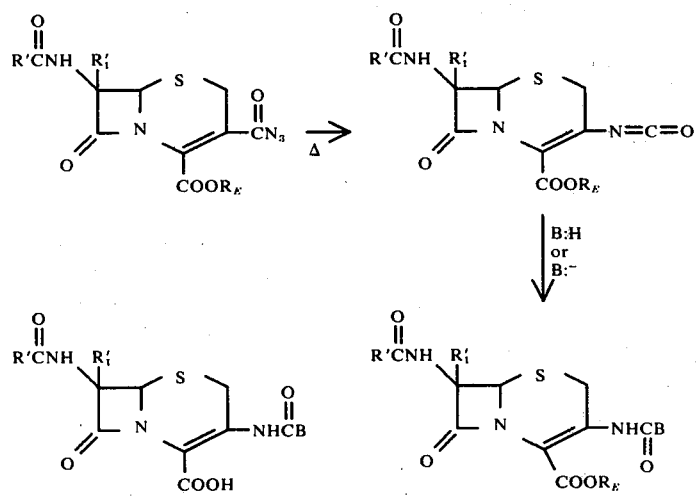

Wherein in the above formulae R', R₁', R₄, R₅, R₆ and R₇ are as defined above, R$_E$ is a carboxylic acid ester protecting group; and B is R₄O—, R₅S—,

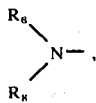

or R₇— where the source of R₇— is R₇MgX, LiR₇ or NaR₇. Thus, the 7-acylamino-3-azidocarbonyl-3-cephem-4-carboxylic acid ester starting material is heated gently, usually in a refluxing inert organic solvent, to provide the corresponding 7-acylamino-3-isocyanato-3-cephem-4-carboxylic acid ester. Such a conversion of or an (alkylthio)carbonylamino group, are prepared from the parent 7-acylamino cephems by any one of a variety of side chain cleavage procedures known in the cephalosporin art. The 7-amino derivative thereby obtained can be reacylated by known techniques to give preferred 7-acylamino side chains for maximum biological activity. Thus, the process for the preparation of the compounds of this invention can be carried out on starting materials having side chains most suitable for the preparative process (because of availability or stability to reaction conditions), and thereafter these side chains can be replaced by other 7-acylamino side chains preferred for maximum biological activity. For example, a 3-azidocarbonyl cephem starting material, derived from readily available cephalothin, has the 2-thienylacetamido side chain which is stable under the reaction conditions employed in the preparation of the compounds of this invention. Although the cephem carboxylic acids of this invention having a 7-(2-thienylacetamido) substituent do exhibit antimicrobial activity, increased activity can be achieved by replacement of the 2-thienylacetyl group with, for example, a 2-formyloxy-2-phenylacetyl, or 2-carboxy-2-phenylacetyl group.

The immediate precursor to the compounds of the present invention is a 7-acylamino-3-azidocarbonyl-2(or 3)-cephem-4-carboxylic acid ester. Hereinbelow, for the purpose of simplicity, the description of the preparation of the compounds of this invention will be presented only from the aspect of employing a 3-azidocarbonyl-2-cephem as the starting material. It should be noted, however, that the preparation is equally successful starting with the analogous 3-azidocarbonyl-3-cephem compounds.

The following reaction scheme is illustrative of the preparation of 7-acylamino-3-azidocarbonyl-2-cephem-4-carboxylic acid esters of Formula III, immediate precursors of the compounds of this invention:

The 7-acylamino-7-methoxy-3-formyl-2-cephem-4-carboxylic acids and ester derivatives thereof can be prepared from the corresponding known 7-acylamino-7-methoxy-3-acetoxymethyl cephem derivatives, for example, 7-methoxy cephalothin, by procduces identical to those described hereinabove for the conversion of non-methoxylated cephalosporins to the respective 3-formyl cephem starting materials.

The next step in the preparation of the intermediate 3-azidocarbonyl cephem compounds is the conversion of the 3-formyl cephem to its corresponding acetal derivative. A cyclic acetal, e.g. that formed by the reaction of ethylene glycol with the 3-formyl cephem, is preferred. The preferred method for acetalization of the 7-acylamino-3-formylcephem compounds comprises reacting the 3-formyl derivative with a large excess of the glyocol in the presence of a catalytic amount of p-toluenesulfonic acid in refluxing benzene. Water is removed from the refluxing reaction mixture by the use of a Dean-Stark trap. After approximately 10 hours, or when water ceases to condense in the Dean-Stark trap, the reaction mixture is cooled and

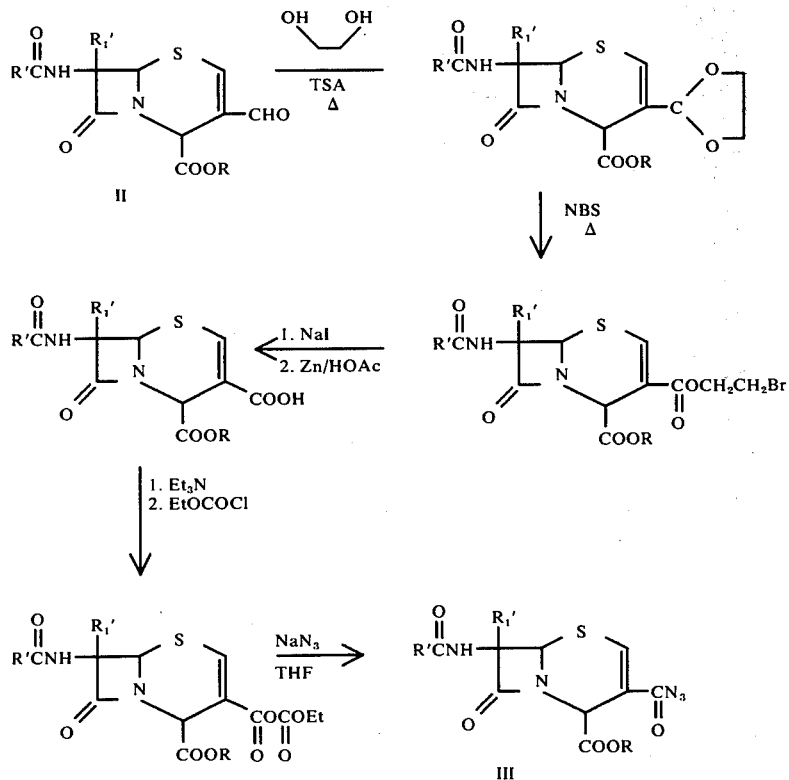

washed with sodium bicarbonate solution. The acetal thereby obtained is conveniently purified by chromatography over silica gel.

Several methods for the preparation of the 3-formyl-2-cephem compounds of Formula II above have been disclosed. These compounds were first described by Woodward et al. [(Journal of the American Chemical Society, 88, 852 (1966) as intermediates in the total synthesis of cephalosporin C. Generally the 3-formyl cephem compounds are prepared by oxidation of the corresponding known 3-hydroxymethyl cephem derivatives with manganese dioxide or chromium trioxide. The use of chromium trioxide as the oxidizing agent, particularly chromium trioxide in sulfuric acid/water, commonly referred to as "Jones Reagent" is preferred. See U.S. Pat. No. 3,351,596.

Oxidation of the ethylene acetal with N-bromosuccinimide in accordance with the procedures described by J. D. Prug and W. D. McCarthy, Tetrahedron Letters, 1351 (1966) provides the corresponding 7-acylamino-3-(2-bromoethoxycarbonyl)-2(or 3) cephem-4-carboxylic acid ester (a cephem-3,4-dicarboxylic acid diester). In general the acetal-diester conversion is carried out by reacting the acetal derivative with 1.0 to 1.2 molar equivalents of N-bromosuccinimide in the presence of a free radical initiator, such as azobisisobutyronitril (AIBN) or benzoyl peroxide, in an inert organic solvent at a temperature between about 40° and 100°C.

The preferred conditions and procedures employed in the preparation of 7-acylamino-3-(2-bromoethoxycarbonyl)-2-cephem-4-carboxylic acid esters, preferred dicarboxylic acid diester intermediates to the compounds of this invention, are summarily delineated in the following description of the preparation of 4'-nitrobenzyl 7-(2-thienylacetamido)-3-(2-bromoethoxycarbonyl-2-cephem-4-carboxylate from the corresponding 3-formyl cephem ethylene acetal: A mixture of 5 mmol. of 4'-nitrobenzyl 7-(2-thienylacetamido)-3-(1,3-dioxolan--2-yl)-2-cephem-4-carboxylate, 5.5 mmol. of N-bromosuccinimide, and 0.05 mmol 1. of azobisisobutyronitrile in 200 ml. of benzene is heated to reflux for 20 to 25 minutes and then cooled and evaporated to dryness. Chromatography of the resultant product mixture on silica gel using a toluene-ethyl acetate gradient provides 4'-nitrobenzyl 7-(2-thienylactamido)-3-(2-bromoethoxycarbonyl)-2-cephem-4- carboxylate.

The aforedescribed 7-acylamino-3-cephem-3,4-dicarboxylic acid diester compounds are key intermediates in the synthesis of the compounds of the present invention. At this stage of the preparation the existing 7-acylamino side chain can easily be cleaved by any one of a variety of amide cleavage procedures. The corresponding 7-amino cephem diester derivatives thereby produced can then be reacylated to provide either intermediates having the 7-acylamido side chain desired for the final products (compounds of this invention) or intermediates wherein the 7-amino group is protected with a benzyloxycarbonyl group, a tert-butoxycarbonyl group or like protecting group. This latter class of intermediates is useful for the preparation of 7-amino-3-acylamino-3-cephem-4-carboxylic acids and esters which cannot be prepared by the standard amide cleavage reactions because of the presence of two amide functional groups on the molecule.

The 7-acylamino side chain of the cephem diester intermediates can be cleaved by any one of a variety of known cleavage procedures to provide the corresponding 7-amino derivatives. Such a cleavage can be carried out by the well known PCl$_5$/pyridine: alcohol: water procedure as described, for example, in U.S. Pat. No. 3,697,515. Alternatively, a nitrosyl chloride cleavage procedure described in U.S. Pat. No. 3,261,832 can be used.

Acylation of the 7-amino-2-cephem-3,4-dicarboxylic acid diesters to provide alternative intermediates to the compounds of the present invention may be carried out by following well-known procedures used for the acylation of other cephalosporin nuclei, such as 7-ACA or 7-ADCA. A preferred method for acylating the nucleus diesters comprises reacting the nucleus diester with an acid chloride derivative corresponding to the desired acyl group in the presence of sodium bicarbonate in tetrahydrofuran at 0° to 5° C. Likewise the 7-amino group can be protected with, for example, a benzyloxycarbonyl or a tert-butoxycarbonyl group by reacting the nucleus diester with the corresponding haloformate, for example, benzylchloroformate (prepared by reacting benzyl alcohol with excess phosgene in an inert organic solvent at 0° to 10° C.) in tetrahydrofuran at 0° to 5° C. in the presence of sodium bicarbonate.

Representative of 2-cephem-3,4-dicarboxylic acid diester intermediates to the compounds of the present invention are:

benzhydryl 7-(2-thienylacetamido)-3-(2-bromoethoxycarbonyl)-2-cepham-4-carboxylate,
tert-butyl 7-phenylacetamido-3-(2-bromoethoxycarbonyl)-2-cephem-4-carboxylate,
4'-methoxybenzyl 7-benzyloxycarbonylamino-3-(2-bromoethoxycarbonyl)-2-cephem-4-carboxylate,
benzhydryl 7-(2-tert-butoxycarbonyl-2phenylacetamido)-3-(2-bromoethoxycarbonyl)-2-cepham-4-carboxylate,
tert-butyl 7-(tert-butoxycarbonylamino)-3-(2-bromoethoxycarbonyl)-2-cephem-4-carboxylate,
benzhydryl 7-(2-formyloxy-2-phenylacetamido)-3-(2-bromoethoxycarbonyl)-2-cepham-4-carboxylate,
4'-methoxybenzyl 7-benzyloxycarbonylamino-3-(2-bromoethoxycarbonyl)-2-cephem-4-carboxylate,
benzhydryl 7-acetamido-3-(2-bromoethoxycarbonyl)-2-cephem-4-carboxylate,
tert-butyl 7-(2,5-dichlorophenylthioacetamido)-3-(2-bromoethoxycarbonyl)-2-cephem-4-carboxylate,
benzhydryl 7-(3-thienylacetamido)-3-(2-bromoethoxycarbonyl)-2-cephem-4-carboxylate, and the corresponding cephem diesters having additionally a 7-methoxy substituent.

Although the C-7 side chains desired for maximum antibiotic activity of cephem acids of this invention can be attached at the cephem-3,4-dicarboxylic acid ester stage of the preparation of the compounds of this invention, it is generally preferred that side chain modification be performed after the C-3 position is functionalized as desired. Thus the side chain on the 3-formyl cephem starting material is not usually modified until the desired conversions at C-3 have been accomplished. It should be noted, however, that side chain modification at the diester stage is advantageous where the final products of the preparation are intended to be 3-acylamino cephems; selective cleavage of the 7-acylamino group can not be accomplished without difficulty on a 3,7-diacylamino substrate. If the 7-amino group were protected with e.g., a 4-nitrobenzyloxycarbonyl group at the diester step in the synthesis, a selective cleavage of such a 7-amino protecting group could be readily achieved after C-3fnctionalization to afford a 7-amino-3-acylamino-3-cephem-4-carboxylic acid ester.

The intermediate 7-acylamino-3-carboxy-2-cephem-4-carboxylic acid ester compounds of the formula

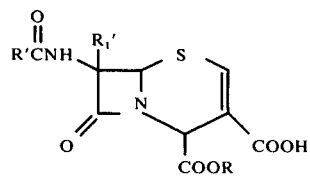

are prepared by deesterification of the corresponding 3-(2bromoethoxycarbonyl) cephem derivatives by a process comprising the conversion of the 2-bromoethyl ester group to the corresponding 2-iodoethyl ester, which group is subsequently removed reductively by treatment with 5to 15 equivalents of zinc and excess acetic acid at 0-5° C. The application of this two-step process for the removal of a 2-bromoalkyl ester group on cephalosporin compounds in particular has been described in Netherlands Patent No. 7,010,475. The 2-iodoethyl esters are derived from the 2-bromoethyl esters by reaction with 1.0-4.0 equivalents of sodium iodide in acetone at 30-40° C. for 15-20 hours. This is a known conversion (Finkelstein reaction) and is accomplished in high yields with primary alkyl bromides.

The deesterification of a 3-(2-bromoethoxycarbonyl) group is, thus, preferably accomplished by (1) conversion to the corresponding 2-iodoethyl ester with 1–4 equivalents of sodium iodide in acetone at 35° for 16 hours; and (2) reductive removal of the resultant iodoethyl group.

The preferred C-4 carboxylic acid ester protecting groups are, as illustrated above, tert-butyl, benzhydrl, dimethylallyl, and 4-methoxybenzyl. Such protecting groups are preferred because of their stability to the reductive cleavage conditions (Zn/HOAc) employed in the removal of the 2-iodoethyl ester functionality. Thus, under such reductive conditions, the C-4 carboxylic acid group remains protected with the tert-butyl, benzhydryl, dimethylallyl, or 4-methoxybenzyl group while the C-3carboxylic acid group is freed for further functionalization, i.e. conversion to the corresponding acyl azide as described hereinbelow. Other commonly used C-4 carboxylic acid protecting ester groups such as 2,2,2-trichloroethyl, 2-iodoethyl or 4-nitrobenzyl, which are removed under reductive conditions, are not, in general, satisfactory at this stage of the preparation of the compounds of the present invention. However, such protecting groups (removable by reduction) and related-oxycarbonyl amine protecting groups may be incorporated in the cephem intermediates at any point in the preparative procedure subsequent to the deesterification of the C-32-iodoethyl ester group of the diester intermediate. It should be noted that in addition to the aforementioned preferred protecting groups other conventional carboxylic acid ester protective groups which are stable to the reductive conditions required for the C-3deesterification step can be employed to protect the C-4 carboxylic acid functionality.

The 3-carboxy-2-cephem-4-carboxylic acid esters, prepared by deesterification of the 3-(2-bromoethoxycarbonyl)-2-cephem-4-carboxylic acid esters, are employed in the preparation of the corresponding 3-azidocarbonyl cephem derivatives, the immediate precursors to the 3-isocyanatocephem compounds of the present invention. The preparation of the acyl azide derivatives from the corresponding carboxylic acids is a straightforward, well-known reaction. It involves the reaction of azide ion with the mixed anhydride or acid halide derivative of a carboxylic acid. Thus, sodium azide or tetramethylguanidinium azide reacts with the acid chloride (prepared preferably by the reaction of oxalyl chloride and the carboxylic acid in the presence of dimethylformamide) or a mixed anhydride derivative (prepared by the reaction of the triethylamine salt of the carboxylic acid and an alkylchloroformate, e.g., methylchloroformate) of a 3-carboxy-2-cephem-4-carboxylic acid ester at room temperature in an inert organic solvent, such as, dioxane, tetrahydrofuran or dimethylformamide to provide the corresponding 3-azidocarbonylcephem intermediate. For example tert-butyl 7-phenoxyacetamido-3-carboxy-2-cephem-4-carboxylate can be converted to the corresponding acylazide derivative by (a) treatment with 1 equivalent of triethylamine and about 1.1 equivalent of isobutylchloroformate in tetrahydrofuran to form the corresponding mixed anhydride and (b) reacting said mixed anhydride in situ with 1 equivalent of tetramethylguanidinium azide.

Exemplary of the 3-azidocarbonyl cephem compounds suitably employed in the preparation of the compounds of the present invention are benzhydryl 7-(tert-butoxycarbonylamino)-3-azidocarbonyl-2-cephem-4-carboxylate,
tert-butyl 7-(3-thienylacetamido)-3-azidocarbonyl-2-cephem-4-carboxylate,
4'-methoxybenzyl 7-(2-formyloxy-2-phenylacetamido)-3-azidocarbonyl-2-cephem-4carboxylate,
benzhydryl 7-phenoxyacetamido-3-azidocarbonyl-2-cephem-4-carboxylate,
tert-butyl 7-benzyloxycarbonylamino-3azidocarbonyl-2-cephem-4carboxylate,
benzhydryl 7-(2-tert-butoxycarbonyl-2-phenylacetamido)-3-azidocarbonyl-2-cephem-4-carboxylate,
4'-methoxybenzyl 7-(2-tert-butoxycarbonylamino-2-phenylacetamido)-3-azidocarbonyl-2-cephem-4-carboxylate,
4'-methoxybenzyl 7-benzyloxycarbonylamino-3-azidocarbonyl-2-cephem-4-carboxylate,
benzhydryl 7-(2-thienylacetamido)-3-azidocarbonyl-2-cephem-4-carboxylate,
benzhydryl 7-(2-chloroacetamido)-3-azidocarbonyl-2-cephem-4-carboxylate,
4'-methoxybenzyl 7-benzamido-3-azidocarbonyl-2-cephem-4-carboxylate,
tert-butyl 7-(2,5-dichlorophenylithioacetamido)-3-azidocarbonyl-2-cephem-4-carboxylate,
tert-butyl 7-[2-tert-butoxycarbonylamino-2-(2-thienyl)acetamido]-3-azidocarbonyl-2-cephem-4-carboxylate,
benzhydryl 7-[2-tert-butoxycarbonylamino-2-(4-hydroxyphenyl)acetamido]-3-azidocarbonyl-2-cephem-4-carboxylate,
4'-methoxybenzyl 7-(2-formyloxy-2-phenylacetamido)-3-azidocarbonyl-2-cephem-4-carboxylate,
benzhydryl 7-[2tert-butoxycarbonylamido-2-(1,4-cyclohexadien-1-yl)acetamido]-3-azidocarbonyl-2-cephem-4-carboxylate, and the corresponding 3-azidocarbonyl cephem compounds having additionally a 7-methoxy substituent.

Pyrolysis of the above described 3-azidocarbonyl cephem compound provides the intermediate 3-isocyanato cephem compounds of this invention which are subsequently converted, by reaction with nucleophic reagents, to the 3-(substituted)carbonylamino cephems. The pyrolysis of the acylazides is generally carried out by refluxing a solution of the azidocarbonyl compound in an inert organic solvent, preferably benzene or toluene. This pyrolytic rearrangement, commonly known as the Curtius rearrangement, is a well-known reaction of acyl azides and has been applied to acyl azide derivatives of many carboxylic acids including aliphatic, alicyclic, heterocyclic, unsaturated and those containing functional groups. Thus the conversion of, for example, 4'-methoxybenzyl 7-(2-formyloxy-2-phenylacetamido)-3-azidocarbonyl-2-cephem-4-carboxylate to 4'-methoxybenzyl 7-(2-formyloxy-2-phenylacetamido)-3-isocyanato-2-cephem-4-carboxylate can be accomplished by gently refluxing a solution of said azidocarbonyl compound in dry benzene for about 30 minutes. The product 3-isocyanatocephem can, thereafter, be isolated simply by evaporation of the reaction solvent, or, if desired, can be reacted in situ with an appropriate nucleophic reagent to provide a 3-(substituted)carbonylamino cephem compound of this invention.

It should be noted that other routes to the intermediate 3-isocyanato cephem compounds of this invention are available. For example, the corresponding hydroxamic acid derivatives of the aforedescribed 3-carboxycephem compounds, give the related 3-isocyanato cephems when subjected to the conditions of the well-known Lossen rearrangement. Alternatively, the preparation of 3-isocyanatocephem derivatives from the corresponding 3-carboxycephems can be achieved using a modified Curtius reaction comprising the reaction of the 3-carboxycephem compound with diphenylphosphoryl azide, an azide transfer reagent, in the presence of triethylamine. Such a modified Curtius reaction is usually carried out in the presence of an alcohol or a thiol which reacts with the intermediate isocyanate as it is formed to provide the corresponding carbamate or thiocarbamate respectively.

As mentioned hereinabove the 3-isocyanatocephem compounds of this invention are intermediates for the preparation of the biologically active cephem compounds of this invention having a substituted carbonylamino group at the C-3 position on the cephem ring. Thus the isocyanate derivatives are reacted with alcohols to give 3-alkoxycarbonylamino, or carbamate, cephems, with thiols to provide cephems having a thiocarbamate at the C-3 position, with primary or secondary amines to provide 3-ureido or 3-(substituted-)ureido cephems, or with Grignard reagents or other carbanionic compounds to provide 3-acylaminocephem derivatives.

Cephems of this invention having a carbamate functionality at C-3 can be prepared by reaction of the 3-isocyanatocephem intermediates with alcohols in an inert organic solvent, e.g., methylene chloride, chloroform, tetrahydrofuran benzene, dioxane, or acetonitrile at room temperature. This is a standard procedure for the preparation of carbamates and is well documented in the chemical literature. Alternatively the 3-alkoxycarbonylamino 3-cephems can be prepared directly from the 7-acylamino-3-carboxy-2(or 3)-cephem-4-carboxylic acid esters by the modified Curtius reaction referred to above. The reaction is generally carried out at elevated temperatures, usually at the reflux temperature of the reaction medium. Reaction time varies from about 10 to about 48 hours depending on the nature of the substrate, the alcohol, and the solvent employed.

Exemplary of the alcohols which may be used in preparing the carbamates of the present invention are methanol, ethanol, propanol, isopropanol, butanol, cyclohexanol, 2-chlorobutanol, 2-pentanol, trichloroethanol, 4-methoxybenzyl alcohol, benzyl alcohol, phenol, and 4-nitrobenzyl alcohol. For example, benzhydryl 7-acetamido-3-isopropoxycarbonylamino2-cephem-4-carboxylate can be prepared by reacting benzhydryl 7-acetamido-3-carboxy-2-cephem-4-carboxylate with about 1.1 equivalents of triethylamine and about 1.1 equivalents of diphenylphosphoryl azide in the presence of 1 to 2 equivalents of isopropanol in refluxing benzene.

The corresponding thiocarbamate derivatives of the present invention are prepared by the same general procedures as described above for the preparation of the 3-alkoxycarbonylamino cephems except that mercaptans (thiols), instead of alcohols, are employed in the preparation. Preferably the thiocarbamates are prepared by reacting a mercaptan with the 3-isocyanato cephem in an inert organic solvent, e.g. methylene chloride, chloroform, dioxane, tetrahydrofuran, benzene, or acetonitrile at room temperature. Representative of the mercaptans which can be employed in prepared in preparing the thiocarbamates of the present invention are methanethiol, ethanethiol, isopropylthiol, 2-butanethiol, hexanethiol, benzylthio, phenylthiol, 2-pentanethiol, 1-butanethiol, and 2-methyl-2-butanethiol. In a representative preparation of a 3-alkylthio)carbonylamino cephem, tert-butyl 7-(2-formyloxy-2phenylacetamido)-3-isocyanato-2-cephem-4-carboxylate is reacted with 1.1 equivalents of ethanethiol in tetrahydrofuran at room temperature for 15 minutes to provide tert-butyl 7-(2-formyloxy-2-phenylacetamido)-3-(ethylthio)carbonylamino-2-cephem-4-carboxylate in high yield.

Illustrative of the aforedescribed cephem carbamate and thiocarbamate esters of the present invention are 4'-methoxybenzyl 7-(2-thienylacetamido)-3-(benzylthio)carbonylamino-2-cephem-4-carboxylate,
benzhydryl 7-(4-chlorophenylacetamido)-3-methoxycarbonylamino-2-cephem-4-carboxylate,
tert-butyl 7-(tert-butyloxycarbonylamino)- 3-(cyclohexylthio)carbonylamino-2-cephem-4-carboxylate,
benzhydryl 7-(2-chloroacetamido)-3-isopropoxycarbonylamino-2-cephem-4-carboxylate,
tert-butyl 7-(phenylthio)acetamido-3-(phenylthiocarbonylamino-2cephem-4-carboxylate,
benzhdryl 7[2-benzyloxycarbonylamino-2-(4-methoxyphenyl)acetamido]-3-(butylthio)carbonylamino-2-cephem-4-carboxylate,
4'-methoxybenzyl 7-(2-formyloxy-2-phenylacetamido)-3-propoxycarbonylamino-2cephem-4-carboxylate,
benzhydryl 7-benzyloxycarbonylamino-3-(methylthio)-carbonylamino-2-cephem-4-carboxylate,
tert-butyl 7(2-chlorophenoxyacetamido)-3-ethoxycarbonylamino-2-cephem-4-carboxylate,
benzhydryl 7-(2-tert-butoxycarbonyl-2-phenylacetamido)-3-phenoxycarbonylamino-2-cephem-4-carboxylate,
benzhydryl 7-propamido-3-(2-chloroethoxycarbonylamino)-2cephem-4-carboxylate,
4-methoxybenzyl 7-(2-formyloxy-2-phenylacetamido)-3-(isopropylthio)carbonylamino-2-cephem-4-carboxylate, tert-butyl 7-(4-methoxybenzyloxycarbonylamino-3-methoxycarbonylamino-2-cephem-4-carboxylate, and the corresponding cephem compounds having additionally a 7-methoxy substituent.

Characteristic of the 3-carbamate and 3-thiocarbamate 2-cephem compound of this invention is their susceptibility to double bond isomerization upon treatment with a basic reagent, e.g. triethylamine, N,N-diethylaniline, N-methylmorpholine and like tertiary amine bases. The 2-cephem carbamates and thiocarbamates of this invention are converted to the corresponding 3-cephems simply by treatment at room temperature with a tertiary amine base in a suitable inert organic solvent, e.g. methylene chloride, choloroform, ethyl acetate, tetrahydrofuran, benzene, acetonitrile or like solvents. Thus the 2-cephem carbamate and thiocarbamate esters, described and illustrated hereinabove, upon treatment with a tertiary amine base are converted to the corresponding 3-cephem ester derivatives, precursors to the biologically active acids of the present invention. The 3-cephem carbamate and thiocarbamate ester derivatives can also be prepared directly from the corresponding 3-isocyanato-2-cephem ester intermediates by reacting said isocyanates with an alcohol or thiol in the presence of a tertiary amine base. Further evincing the characteristic base catalyzed rearrangement of the 2-cephem carbamates is the aforedescribed modified Curtius rearrangement wherein a 3-carboxy-2-cephem-4-carboxylic acid ester is converted, via the corresponding 3-azidocarbonyl and 3-isocyanato-2-cephem compounds to a 3-cephem carbamate ester of this invention by treatment of the 3-carboxy cephem with triethylamine and diphenylphosphoryl azide in the presence of an alcohol.

The 3-cephem carbamate and thiocarbamate esters of this invention can alternatively be prepared directly by reacting the corresponding aforesdescribed 3-isocyanato-3-cephem intermediates with alcohols and thiols respectively. However, considering the ease of 2-cephem to 3-cephem conversion in the product compounds and the ready availability of 2-cephem starting materials, it preferred that the preparation of the compounds of this invention including those described hereinafter, be carried out with 2-cephem intermediates, thus avoiding the somewhat more burdensome standard oxidation-reduction steps earlier in the preparative procedure.

The 3-carbamate derivatives, particularly those derived from 3-isocyanate cephems and 4-nitrobenzyl or 4-methoxybenzyl alcohol, are useful not only as intermediates to the corresponding biologically active cephem acids, but are also useful intermediates for the preparation of the cephems of this invention having an amino group at C-3. Thus benzhydryl 7-acetamido-3-(4-nitrobenzyloxycarbonylamino)-3-cephem-4-carboxylate, upon reduction with hydrogen in the presence of a palladium on carbon catalyst, provides benzhydryl 7-acetamido-3-amino-3-cephem-4-carboxylate in high yield. Treatment of benzhydryl 7-phenylacetamido-3-(4-methoxybenzyloxycarbonylamino)-3-cephem-4-carboxylate with trifluoroacetic acid in the presence of anisole provides the active 7-phenylacetamido-3-amino-3-cephem-4-carboxylic acid. Alternatively a 7-acylamino-3-amino-3cephem-4-carboxylic acid can be prepared by deesterification of the corresponding 3-amino-3-cephem-4-carboxylic acid ester. For example, 4'-methoxybenzyl 7-(2-hydroxy-2-phenylacetamido)-3amino-3-cephem-4carboxylate, upon treatment with trifluoroacetic acid in the presence of anisole, provides the corresponding 3-amino cephem acid.

Cephems of this invention having a ureido or substituted ureido group at the 3-position on the cephem ring are prepared from the corresponding 3-isocyanato-2(or 3)-cephem intermediates of this invention by reacting the cephem isocyanates with ammonia, primary amines, or secondary amines. The reaction of isocyanates with amine compounds to provide urea or substituted ureas is a known reaction of isocyanates and is well documented in the chemical literature. The reaction is preferably carried out at or near 0° C. in an inert organic solvent, e.g. benzene, toluene, methylene chloride, chloroform, tetrahydrofuran, dioxane, ethyl acetate, or acetonitrile by reacting the cephem isocyanate with about 1 to 5 equivalents of an amine compound. This reaction, as are many of the preparations described herein, is preferably carried out under an argon atmosphere. However, other somewhat less stringent routine experimental procedures designed to maintain anhydrous reaction conditions can be employed without adversely affecting reaction yields.

The reaction of amines with both 3-isocyanato-2-cephem and 3-isocyanato-3-cephem intermediates provides only 3-(substituted)ureido-3-cephem compounds. The 2-cephem compounds are not isolated. This result is not unexpected in light of the aforedescribed base catalyzed rearrangement of other 3-(substituted)carbonylamino-2-cephems.

Exemplary of the amine reagents which can be reacted with the cephem isocyanates to provide 3-(substituted)ureido-3-cephem esters are ammonia; primary amines such as methylamine, ethylamine, butylamine, cyclohexylamine, benzylamine, and aniline; secondary amines such as dimethylamine, diisopropylamine, di-n-butylamine, N-methylaniline, benzylethylamine, isopropylmethylamine, and dibensylamine; and cyclic amines such as piperidine, morpholine and pyrrolidine.

Benzhydryl 7-phenylacetamido-3-isocyanato-2-cephem-4-carboxylate reacts with 2 equivalents of isopropylamine in tetrahydrofuran at 0° for approximately 1 hour to provide benzhydryl 7-phenylacetamido-3-isopropylureido-3-cephem-4-carboxylate. Likewise morpholine reacts under similar conditions with tert-butyl 7-(2-thienylacetamido)-3-isocyanato-2-cephem-4-carboxylate to provide tert-butyl 7-(2-thienylacetamido)-3-morpholinocarbonylamino-3-cephem-4-carboxylate. When 4'-methoxybenzyl 7-(tert-butoxycarbonylamino)-3-isocyanato-2-cephem-4carboxylate is reacted with 2.5 equivalents of N-methylaniline in methylene chloride at 0° for about 1 hour, the product isolated, after chromatography, is 4'-methoxybenzyl 7-(tert-butoxycarbonylamino)-3-(N-methyl-N-phenylureido)-3-cephem-4-carboxylate.

Representative of the 3-(substituted)ureido-3-cephem-4-carboxylic acid esters of this invention available by the hereinabove described procedures are:

benzhydryl 7-[(2,5-dichlorophenylthio)acetamido]-3-ureido-3-cephem-4-carboxylate.
benzhydryl 7-(2-formyloxy-2-phenylacetamido)-3-piper-idinocarbonylamino-3-cephem-4-carboxylate,
4'-methoxybenzyl 7-acetamido-3-benzylureido-3-cephem-4-carboxylate,
tert-butyl 7-benzyloxycarbonylamino)3-pentylureido-3-cephem-4-carboxylate,
tert-butyl 7-(2,5-dichlorophenylthio)acetamido-3-phenylureido-3-cephem-4-carboxylate,
4'-methoxybenzyl 7-phenoxyacetamido-3-p-tolyureido-3-cephem-4-carboxylate,
tert-butyl 7-(2-furylacetamido)-3-(N,N-dibenzylureido)-3-cephem-4-carboxylate,
benzhydryl 7 -chloroacetamido-3-(N-propyl-N-methylureido)-3-cephem-4-carboxylate,
benzhydryl 7-(2-benzhydryloxycarbonyl-2-phenylacetamido)-3-cyclohexylureido-3-cephem-4-carboxylate,
4-methoxybenzyl 7-(2-formyloxy-2-phenylacetamido)-3-(N,N-dimethylureido-3-cephem-4-carboxylate,
and the corresponding cephem compounds having additionally a 7-methoxy substituent.

Carbanionic compounds, e.g. Grignard reagents, organolithium compounds, and sodium or lithium salts of activated hydrogen compounds, react at low temperature with the 3-isocyanato cephems of this invention to provide the corresponding 3-acylamino cephem compounds. The reaction with carbanionic compounds of this nature to provide amide derivatives is a well known reaction of organic isocyanates. Because of the susceptibility of the β-lactam functionality of cephem compounds to nucleophilic attack by carbanionic reagents, the preparation of the 3-acylamino cephems of this invention is preferably carried out at temperatures lower than those at which amide forming reactions are usually performed. The reaction of Grignard reagents or other carbanionic compounds with 3-isocyanato cephems of the present invention is preferably carried out in an inert organic solvent, e.g. tetrahydrofuran, at temperatures ranging from about −20° to about −75° C. Any excess of the carbonionic reagent is destroyed before the mixture is allowed to warm to room temperature by treatment of the reaction mixture with an excess of aqueous acid. Such treatment serves also to hydrolyze the intermediate organomagnesium, organolithium, or organosodium salts, to provide the 3-acylamino-3-cephem esters of the present invention.

Exemplary of the carbonionic reagents which may be employed to prepare the 3-acylamino-3-cephem esters of this invention are Grignard reagents, e.g. ethylmagnesium bromide, benzylmagnesium bromide, methylmagnesium bromide, hexylmagnesiumbromide, phenylmagnesium bromide or the like; organolithium reagents such as methyllithium, n-butyllithium or the like; and sodium or lithium derivatives of activated hydrogen compounds obtained by reacting sodium or lithium hydride or like bases with compounds having a proton on a carbon atom alpha to one or more electron withdrawing groups, e.g. cyano, carbonyl, alkoxycarbonyl, halo, nitro or the like. Included in this latter class of carbanionic reagents are the sodium or lithium derivatives of diethylmalonate, dimethylmalonate, methyl cyanoacetate, ethyl acetoacetate, ethyl bromoacetate and like compounds.

As in the case of the aforedescribed reaction of amines with the 3-isocyanato-2-cephems, the reaction of such isocyanates with carbanionic reagents is accompanied by the rearrangement of the double bond in the cephem ring. Thus, benzhydryl 7-benzyloxycarbonylamino-3-isocyanato-2-cephem-4-carboxylate reacts with 1.1 equivalents of sodium diethylmalonate in tetrahydrofuran at −20° C. over a 5 minute period, to provide after hydrolysis with about 3 equivalents of 1N.HCl, benzhydryl 7 -benzyloxycarbonylamino-3-di(ethoxycarbonyl)acetamido-3-cephem-4-carboxylate. Likewise tert-butyl 7-(3-chlorophenylacetamido)-3-isocyanato-2-cephem-4carboxylate reacts with about 1.1 equivalents of isopropylmagnesium bromide in tetrahydrofuran at about −70° C. over a 30 minute period to give, upon acid hydrolysis, tert-butyl 7-(2-chlorophenylacetamido)-3-(2-methyl-propionamido)-3-cephem-4-carboxylate. The reaction of methyllithium with 4-methoxybenzyl 7-acetamido-3-isocyanato-3-cephem-4-carboxylate under similar conditions yields 4-methoxybenzyl 7-acetamido-3-acetamido-3-cephem-4-carboxylate.

Representative of the 3-acylamino-3-cephem esters of the present invention are:

benzhydryl 7-tert-butoxycarbonylamino-3-phenylacetamido-3-cephem-4-carboxylate,
benzhydryl 7-(phenylthio)acetamido-3-butyramido-3-cephem-4-carboxylate,
tert-butyl 7-(4-chlorophenoxyacetamido)-3-phenylacetamido-3-cephem-4-carboxylate,
4'-methoxybenzyl 7-(4-nitrobenzyloxycarbonylamino)-3-propionamido-3-cephem-4-carboxylate,
tert-butyl 7-(2-thienylacetamido)-3-benzamido-3-cephem-4-carboxylate,
benzhydryl 7-(2-formyloxy-2-phenylacetamido)-3-di(ethoxycarbonyl)acetamido-3-cephem-4-carboxylate, and the corresponding cephem compounds having additionally a 7-methoxy substituent.

Conversion of the above described cephem-4-carboxylic acid esters having a substituted carbonylamino group at C-3 to the corresponding biologically active 3-cephem-4-carboxylic acids of this invention is accomplished by conventional methods, the specific method employed being dependent upon the particular ester protecting group present. As has been exemplified hereinabove, the preferred carboxylic acid esters protecting groups are tert-butyl, benzhydryl, dimethylallyl and 4-methoxybenzyl. These groups are readily removed by treatment with an acid such as trifluoroacetic acid, or formic acid usually in the presence of a carbonium ion stabilizer such as anisole. It should be noted that these techniques can likewise be employed to remove like protecting groups which may be present elsewhere in the cephem compounds. Thus an amine function, protected with a tert-butoxycarbonyl group or a 4-methoxybenzyloxycarbonyl group can be deblocked by dissolution of the protected compound in a mixture of equal volumes of anisole and trifluoroacetic acid at 0° C. Benzhydryl 7-(2-tert-butoxycarbonyl-2-phenylacetamido)-3-acetamido-3-cephem-4-carboxylate is under similar conditions converted to 7-(2-carboxy-2-phenylacetamido)-3-acetamido-3-cephem-4-carboxylic acid.

Representative of the biologically active 7-acylamino-3-(substituted)carbonylamino-3-cephem-4-carboxylic acids of the present invention are the following compounds:

7-(2-amino-2-phenylacetamido)-3-methoxycarbonylamino-3-cephem-4-carboxylic acid,
7-(2-chlorophenoxyacetamido)-3-(benzylthio)carbonylamino-3-cephem-4-carboxylic acid,
7-acetamido-3-acetamido-3-cephem-4-carboxylic acid,
7-(2-furylacetamido)-3-phenylureido-3-cephem-4-carboxylic acid,
7-(5-tetrazolylacetamido)-3-(ethylthio)carbonylamino-3-cephem-4-carboxylic acid,
7-propionamido-3-(N,N-diethylureido)-3-cephem-4-carboxylic acid,
7-(2-formyloxy-2-phenylacetamido)-3-tolylureido-3-cephem-4-carboxylic acid,
7-(2-thiazolylacetamido)-3-benxyloxycarbonylamino-3-cephem-4-carboxylic acid,
7-(3-nitrobenzamido)-3-(butylthio)carbonylamino-3-cephem-4-carboxylic acid,
7-phenoxyacetamido-3-propionamido-3-cephem-4-carboxylic acid,
7-(3-thienylacetamido)-3-(N-methyl-N-benzylureido)-3-cephem-4-carboxylic acid,
7-chloroacetamido-3-benzamido-3-cephem-4-carboxylic acid,
7-(2-hydroxy-2-phenylacetamido)-3-isopropoxycarbonylamino-3-cephem-4-carboxylic acid, 7-(2,5-dichlorophenylthioacetamido)-3-cyclohexyloxycarbonylamino-3-cephem-4-carboxylic acid,
7-benzamido-3-ureido-3-cephem-4-carboxylic acid,
7-[2-formyloxy-2-(4-hydroxyphenyl)acetamido]-3-isopropylureido-3-cephem-4-carboxylic acid,
7-(4-chlorophenylacetamido)-3-acetamido-3-cephem-4-carboxylic acid,
7-[2-amino-2-(1,4-cyclohexadienyl)acetamido]-3-(pentylthio)carbonylamino-3-cephem-4-carboxylic acid,
7-(2-carboxy-2-phenylacetamido)-3-ethoxycarbonylamino-3-cephem-4-carboxylic acid,
7-(3-furylacetamido)-3-benzylureido-3-cephem-4-carboxylic acid,
7-(4-methoxyphenylacetamido)-3-(methylthio)carbonylamino-3-cephem-4-carboxylic acid,
7-acetamido-3-di(methoxycarbonyl)acetamido-3-cephem-4-carboxylic acid,
7-(2-formyloxy-2-phenylacetamido)-3-di(ethoxycarbonyl)acetamido-3-cephem-4-carboxylic acid,
7-(2-thienylacetamido)-3-propylureido-3-cephem-4-carboxylic acid,
7-(2-amino-2-phenylacetamido)-3-(2-methylpropoxycarbonylamino-3-cephem-4-carboxylic acid,
7-(4-trifluoromethylphenylacetamido)-3-(N,N-dimethylureido)-3-cephem-4-carboxylic acid,
7-[2-amino-2-(4-hydroxyphenyl)acetamido]-3-phenylacetamido-3-cephem-4-carboxylic acid, and the corresponding cephem compounds having additionally a 7-methoxy substituent.

As mentioned hereinbefore, the process for the preparation of the compounds of the present invention can be carried out on starting materials having side chains most preferred for the preparative process (because of availability or stability to reaction conditions) and thereafter such side chains can be replaced by other 7-acylamino side chains most preferred for maximum biological activity. Such side chain modifications are most conveniently carried out at either one of two points in the preparation of the active cephem acids of this invention. The modifications can be carried out on the intermediate cephem 3,4-dicarboxylic acid diesters as discussed hereinabove or on the product 3-(substituted)carbonylamino-3-cephem-4-carboxylic acid esters of this invention. Intermediate products in the modification of the 7-acylamido group in the aforedescribed 3-(substituted)carbonylamino-3-cephem esters are the corresponding 7-amino-3-(substituted) carbonylamino-3-cephem-4-carboxylic acid esters, also compounds of this invention. With the exception of the 7-amino-3-acylaminocephems of this invention the 7-amino-3-(substituted)carbonylamino cephem esters are generally prepared by applying any one of a variety of known amide cleavage reactions to the respective 7-acylamino compounds. For example, the 7-acylamino-3-(substituted)-carbonylamino-3-cephem-4-carboxylic acid esters can be cleaved by the well known PCl₅/pyridine:alcohol:water procedure described hereinabove in the discussion of the preparation of intermediates to the compounds of this invention. Thus, tert-butyl 7-phenylacetamido-3-(4-methoxybenzyloxycarbonylamino)-3-cepehm-4-carboxylate is converted to tert-butyl 7-amino-3-(4-methoxybenzyloxycarbonylamino)-3-cephem-4-carboxylate by (a) reacting the 7-acylamino cephem with about 1.0 to 1.2 equivalents of phosphorous pentachloride and pyridine at room temperature in an inert organic solvent, preferably methylene chloride; (b) reacting the imino chloride intermediate thereby formed with isobutanol at low temperature (−10° C) to provide the corresponding imino ether; and (c) hydrolyzing the imino ether with water. Under similar conditions 4'-methoxybenzyl 7-(2-thienylacetamido)-3-(N,N-dimethylureido)-3-cephem-4-carboxylate is converted to 4'-methoxybenzyl 7-amino-3-(N,N-dimethylureido)-3-cephem-4-carboxylate.

An amide cleavage procedure is, however, not applicable to the preparation of 7-amino-3-acylamino-3-cephem-4-carboxylic acid esters of this invention, since the C-3 acylamino group would also be attacked under such reaction conditions. The 7-amino- 3-acylamino cephem esters off this invention are therefore preferably prepared from the respective C-7 carbamate derivatives. For example, benzhydryl 7-(4-nitrobenzyloxycarbonylamino)-3-acetamido-3-cephem-4-carboxylate is hydrogenated in the presence of a 5 percent palladium on carbon catalyst to provide, after acidification, benzhydryl 7-amino-3-acetylamino-3-cephem-4-carboxylate.

Representative of the 7-amino-3-(substituted)-carbonylamino-3-cephem-4-carboxylic acid esters of this invention are the following:

tert-butyl 7-amino-3-isopropoxycarbonylamino-3-cephem-4-carboxylate,
benzhydryl 7-amino-3-(cyclohexylthio)carbonylamino-3-cephem-4-carboxylate,
4'-methoxybenzyl 7-amino-3-phenylureido-3-cephem-4-carboxylate,
benzhydryl 7-amino-3-phenylacetamido-3-cephem-4-carboxylate,
4'-methoxybenzyl 7-amino-3-benzyloxycarbonylamino-3-cephem-4-carboxylate,
tert-butyl 7-amino-3-di(methoxycarbonyl)acetamido-3-cephem-4-carboxylate,
benzhydryl 7-amino-3-isopropylureido-3-cephem-4-carboxylate,
benzhydryl 7-amino-3-(phenylthio)carbonylamino-3-cephem-4-carboxylate,
4'-methoxybenzyl 7-amino-3-methoxycarbonylamino-3-cephem-4-carboxylate,
tert-butyl 7-amino-3-acetamido-3-cephem-4-carboxylate, and the corresponding cephem compounds having additionally a 7-methoxy substituent.

The nucleus acids, comprising 7-amino-3-(substituted)carbonylamino-3-cephem-4-carboxylic acids are preferably prepared from their respective ester derivatives by the aforedescribed deesterification techniques. These amino acid compounds are isolated either as their zwitterions or, alternatively, as their acid addition or alkali metal salts, depending on the pH of the medium from which they are isolated.

Illustrative of the nucleus acids, compounds of the present invention useful for preparing active antibiotic compounds of this invention are the following:

7-amino-3-ethoxycarbonylamino-3-cephem-4-carboxylic acid,
7-amino-3-toluidinocarbonylamino-3-cephem-4-carboxylic acid,
7-amino-3-(phenylthio)carbonylamino-3-cephem-4-carboxylic acid,
7-amino-3-propionamido-3-cephem-4-carboxylic acid, 7-amino-3-(2-butoxycarbonylamino)-3-cephem-4-carboxylic acid 7-amino-3-(benzylthio)carbonylamino-3-cephem-4-carboxylic acid, 7-amino-3-morpholinocarbonylamino-3-cephem-4-carboxylic acid, 7-amino-3-methoxycarbonylamino-3-cephem-4-carboxylic acid, and the corresponding cephem compounds having additionally a 7-methoxy substituent.

The nucleus acids and nucleus esters described hereinabove are useful intermediates for the preparation of those biologically active 7-acylamino-3-(substituted)-carbonylamino-3-cephem-4-carboxylic acids of the present invention wherein the 7-acylamino group is not a particularly preferred group for the process of preparing cephems wth a (substituted) carbonylamino function of C-3, but which is preferred for antimicrobial activity.

Acylation of the nucleus acids or nucleus esters may be carried out by following well-known conventional procedures used for the acylation of other cephalosporin nuclei, such as 7-ACA or 7-ADCA.

Illustrative of preferred substituted cephalosporin antibiotics of the present invention available by techniques discussed hereinbefore are 7-(2-formyloxy-2-phenylacetamido)-3-piperidinocarbonylamino-3-cephem-4-carboxylic acid, 7-(2-amino-2-phenylacetamido)-3-(benzylthio)carbonylamino-3-cephem-4-carboxylic acid, 7-[2-amino-2-(4-hydroxyphenyl)acetamido]-3-ethoxycarbonylamino-3-cephem-4-carboxylic acid, 7-(2-tert-butoxycarbonyl-2-phenylacetamido)-3-ethylureido-3-cephem-4-carboxylic acid, 7-(2-hydroxy-2-phenylacetamido)-3-(4-nitrobenzyloxycarbonylamino)-3-cephem-4-carboxylic acid, 7-[2-amino-2-(2-thienyl)acetamido]-3-phenylacetamido-3-cephem-4-carboxylic acid, 7-(2-thienylacetamido)-3acetamido-3-cephem-4-carboxylic acid, 7-(2-formyloxy-2-phenylacetamido)-3-morpholinocarbonylamino-3-cephem-4-carboxylic acid, 7-(2,5-dichlorophenylthioacetamido)-3-(methylthio)carbonylamino-3-cephem-4-carboxylate, 7-phenoxyacetomido-3-methoxycarbonylamino-3-cephem-4-carboxylate, 7-(2-amino-2-phenylacetamido)-3-acetamido-3-cephem-4-carboxylic acid, 7-(2-hydroxy-2-(4-chlorophenyl) acetamido-3-(cyclohexylthio)carbonylamino-3-cephem-4-carboxylic acid, 7-(2-benzyloxy-2-phenylacetamido)-3-benzyloxycarbonylamino-3-cephem-4-carboxylic acid, 7-(2-carboxy-2-phenylacetamido)-3-di(methoxycarbonyl) acetamido-3-cephem-4-carboxylic acid, 7-(2-formyloxy-2-phenylacetamido-3-methylureido-3-cephem-4-carboxylic acid, 7-(2-carboxyphenylacetamido)-3-(phenylthio)carbonylamino-3-cephem-4-carboxylic acid, 7-(2-hydroxy-2-phenylacetamido)-3-(N-cyclohexyl-N-methylureido)-3-cephem-4-carboxylic acid, 7-[2-amino-2-(4-methoxyphenylacetamido)]-3-butyramido-3-cephem-4-carboxylic acid, 7-[2-(4-chlorophenyl)acetamido]-3-propoxycarbonylamino-3-cephem-4-carboxylic acid, 7-[2-formyloxy-2-(4-methoxyphenylacetamido)]-3-(N,N-dimethylureido)-3-cephem-4-carboxylic acid, and the corresponding cephem compounds having additionally a 7-methoxy substituent.

The free acids of this invention form carboxylate salts with any of a variety of inorganic and organic bases. Pharmaceutically acceptable carboxylate salts are formed by reacting the free acids with bases such as sodium hydroxide, sodium carbonate, potassium hydroxide, potassium 2-ethylhexanoate, calcium carbonate, ethylamine, 2-hydroxyethylamine and like bases. Preferred carboxylate salt forms are the alkali metal salts. A preferred base for the formation of the potassium salt is potassium 2-ethylhexanoate. The carboxylate salts can be converted to the free acids by acidification. The free acids and their carboxylate salts can be considered as equivalent for the purpose of this invention.

The cephem antibiotics of this invention are relatively non-toxic substances which are useful in combatting infections in warm blooded mammals when administered parenterally in a pharmaceutically effective non-toxic dosage form. The 7-acylamino-3-(substituted)carbonylamino-3-cephem-4-carboxylic acids of this invention can be formulated into liquid pharmaceutical form, e.g. in water, isotonic saline, or the like, and administered by intramuscular injections or by intravenous administration procedures to provide dosages of from about 125 mg. to 16 grams a day depending on the patient's body weight, the disease condition being treated, and other factors of concern to the patient's physician. In controlling infections in particular hosts, repeated administration of smaller doses may suffice, while in other instances larger non-toxic doses may be administered to achieve the desired control. Such variations are well within the techniques of those skilled in the art. The antibiotic compounds of this invention can be administered in the free acid form or in the form of a pharmaceutically acceptable non-toxic salt, such as the sodium or potassium salt.

The following examples are provided to further illustrate this invention. It is not intended that this invention be limited in scope by reason of any of these examples. In the following examples, infrared absorption spectra and nuclear magnetic resonance spectra are abbreviated ir and nmr respectively. Only the ir absorptions attributable to the carbonyl function of the β-lactam ring and other significant functionalities giving rise to conspicuous ir absorptions are reported. The nuclear magnetic resonance spectra were obtained on a Varian Associated T-60 Spectrometer using tetramethylsilane as the reference standard. The chemical shifts are expressed in δ values in parts per million (ppm) and coupling constants (J) are expresses as Hz in cycles per second.

PREPARATION 1

Benzhydryl 7-(2-thienylacetamido)-3-formyl-2-cephem-4-carboxylate

To a slurry of 7-(2-thienylacetamido-3-hydroxymethyl-2-cephem-4-carboxylic acid (23.6 g., 67 mmol.) in 500 ml. ethyl acetate was added dropwise a solution of diphenyldiazomethane (19.4 g., 0.1 mole) in 50 ml. ethyl acetate. The reaction mixture was refluxed for 15 minutes, cooled to room temperature and evaporated in vacuo to dryness. The residue was washed with 1 liter of 1:1 -ethyl ether:petroleum ether giving a pink solid:benzhydryl 7-(2-thienylacetamido)-3-hydroxymethyl-2-cephem-4-carboxylate (33 g., 94.2% yield).

To a stirred solution of the benzhydryl ester in 1 liter of acetone was added dropwise 33.6 ml. (76 mmol., 1.2 eq.) of chromic acid. The reaction mixture was allowed to stir at room temperature for 8 minutes. Isopropyl alcohol (35 ml.) was then added, and the mixture was stirred for an additional 5 minutes. The reaction mixture was evaporated in vacuo to low volume and extracted with ethyl acetate (2 × 400 ml.). The organic extracts were combined and washed successively with water (4X), sodium bicarbonate solution, water, 1N.HCl, and sodium chloride solution, and then dried ($Na_2SO_4$). Evaporation in vacuo to dryness gave 31.3 g. (95.4%) of crude benzhydryl 7-(2-thienylacetamido)-3-formyl-2-cephem-4-carboxylate which was purified either by crystallization from toluene (43% yield) or by chromatography on silica gel (50 g.) using a benzene-ethyl acetate gradient (22 g., 62% yield). The product was recrystallized from methylene chloride-hexane to give white needles (mo 159°–150° C.): ir ($CHCl_3$) 1785 ($\beta$-lactam C=O), 1680 (amide C = O), and 2830 $cm^{-1}$ (formyl C = O); nmr ($CDCl_3$) $\delta$3.80 (s, 2, side chain $CH_2$), 5.12 (d, 1, J = 4.0 Hz, $C_6$—H), 5.40 (q, 1, J =4.0 and 8.0 Hz, $C_7$—H), 5.51 (s, 1, $C_4$—H), and 9.20 (s, 1, CHO).

Analysis Calcd. for $C_{27}H_{22}N_2O_5S_2$: C, 62.53; H, 4.28; N, 5.40; Found: C, 62.33; H, 4.19; N, 5.17.

PREPARATION 2

Benzhydryl 7-(2-thienylacetamido)-3-(1,3-dioxolan-2-yl)-2-cephem-4-carboxylate

Benzhydryl 7-(2-thienylacetamido)-3-formyl-2-cephem-4-carboxylate (21.5 g., 41.5 mmol.) was combined with 11.6 ml. of ethylene glycol (0.2 mole) and toluenesulfonic acid monohydrate (0.197 g., 1.04 mmol.) in 500 ml. benzene. The mixture was refluxed for 10 hours using a Dean-Stark trap (1.5 ml. water coolected), cooled, and evaporated in vacuo to dryness. The product was taken up in ethyl acetate and washed successively with sodium bicarbonate solution (2X), water (2X) and sodium chloride solution and solution and subsequently dried over $Na_2SO_4$. Evaporation in vacuo to dryness gave a product which was chromatographed on 40 g. of silica gel using a benzene-ethyl acetate gradient. Crystallization of the purified product from methylene chloridehexane gave benzhydryl 7-(2-thienylacetamido-3-(1,3-dioxolan-2-yl)-2-cephem-4-carboxylate as colorless needles (15.07 g., 64.2%: mp 142°–143°: ir ($CHCl_3$) 1780 $cm^{-1}$ ($\beta$-lactam C=O); nmr ($CDCl_3$) $\delta$3.3–3.9 (m, 4, —$CH_2$—$CH_2$—), 3.83 (s, 2, side chain $CH_2$), 5.10 (d, 1, J =4.0 Hz, $C_6$—H), 5.17 (s, 1, acetal CH), 5.21 (s, 1, $C_4$—H) and 5.45 (q, 1, J =4.0 and 8.0 Hz, $C_7$—H).

Analysis Calcd. for $C_{29}H_{26}O_6S_2$: C, 61.69; H, 4.66; N, 4.98; Found C, 61.60; H, 4.43; H, 5.10.

PREPARATION 3

Benzhydryl 7-(2-thienylacetamido)-3-(2-bromoethoxycarbonyl)-2-cephem-4-carboxylate Benzhydryl 7-(2-thienylacetamido)-3-(1,3-dioxolan-2-yl)-2-cephem-4-carboxylate (15.07 g., 26.8 mmol.) was combined with N-bromosuccinimide (5.25 g., 29.5 mmol.) and azobisisobutyronitrile (36.5 mg., 0.26 mmol., .01 eq.) in 1200 ml. of benzene. The mixture was gently refluxed for 20 minutes, cooled, and evaporated in vacuo to dryness to give a dark colored product. Chromatography on 30 g. of silica gel using a toluene-ethyl acetate gradient provided 7.61 g. (44.4%) of benzhydryl 7-(2-thienylacetamido)-3-(2-bromoethoxycarbonyl)-2-cephem-4-carboxylate: mp 129°–130°; ir ($CHCl_3$) 1785 $cm^{-1}$ ($\beta$-lactam C = O); nmr ($CDCl_3$ $\delta$3.25 (t, 2, J = 6.0 Hz, $CH_2Br$), 3.38 (s, 2, side chain $CH_2$), 4.30 (t, 2, J = 6.0 Hz, O—$CH_2$—) 4.95 (d, 1, J=4.0 Hz, $C_6$—H), 5.45 (q, 1, J = 4.0 and 8.0 Hz, $C_7$—H), 5.50 (s, 1, $C_4$—H) and 7.80 (s, 1, $C_2$—H).

Analysis Calcd. for $C_{29}H_{25}BrN_2O_6S_2$: C, 54.29; N, 3.93; N, 4.37; Found: C, 54.22; H, 3.90; N, 4.27.

PREPARATION 4

Benzhydryl 7-(2-thienylacetamido)-3-(2-iodoethoxycarbonyl)-2-cephem-4-carboxylate Benzhydryl 7-(2-thienylacetamido)-3-(2-bromoethoxycarbonyl)-2-cepham-4-carboxylate (7.61 g., 12 mmol.) was combined with sodium iodide (6.75 g., 45 meq.) in 100 ml. acetone. The reaction mixture was degassed and then heated to 35° with stirring for 16 hours. The reaction mixture was filtered and evaported to dryness. The residue was dissolved in ethyl acetate and washed with water (3X) and brine and dried ($Na_2SO_4$). Evaporation in vacuo to dryness provided 7.78 g. (95.5%) of benzhydryl 7-(2-thienylacetamido)-3-(2-iodoethoxycarbonyl)-2-cephem-4-carboxylate: ir ($CDCl_3$) 1785 $cm^{-1}$ ($\beta$-lactam C = O); nmr ($CDCl_3$) $\delta$2.96 (t, 2, J = 7.0 Hz, $CH_2I$), 3.80 (s, 2, side chain $CH_2$), 4.24 (t, 2, J = 7.0 Hz, —$OCH_2$—), 4.95 (D, 1, J =4.0 Hz, $C_6$—H), 5.24 (q, 1, J = 4.0 Hz, $C_7$—H, rest of the signal covered by $C_4$—H), 5.50 (s, 1, $C_4$—H), and 7.80 (s, 1, $C_2$—H).

PREPARATION 5

Benzhydryl 7-(2-thienylacetamido)-3-(2-bromoethoxycarbonyl)-3-cephem-4-carboxylate To a cooled (5° C.) stirred solution of benzhydryl 7-(2-thienylacetamido)-3-(2-bromoethoxycarbonyl)-2-cephem-4-carboxylate (0.29 g., 0.453 mmol.) in 30 ml. chloroform was added 85% m-chloroperbenzoic acid (0.101 g., 0.497 mmol.) in 3 ml. chloroform. The mixture was allowed to stir with cooling for 30 minutes, and then was washed with sodium bicarbonate solution (2X) and sodium chloride solution and dried over $Na_2SO_4$. Evaporation in vacuo gave 301 mg. of the $\Delta^3$ sulfoxide. The sulfoxide was dissolved in 25 ml. dimethylformamide, cooled briefly, and then treated with 0.06 ml. (0.678 mmol., 1.5 eq.) phosphorous trichloride. The mixture was allowed to stire at ambient temperature for 30 minutes. Ethyl acetate was added to the reaction mixture, and then it was washed successively with water (2X), aqueous sodium bicarbonate (2X), and brine. The organic layer was dried over anhydrous $Na_2SO_4$ and evaporated in vacuo to dryness. The crude product was chromatographed on 5 g. of silica gel using a benzene-ethyl acetate gradient providing benzhydryl 7-(2-thienylacetamodio)-3-(2-bromoethoxycarbonyl)-3-cephem-4-carboxylate (0.154 g., 53%) as a colorless solid: ir ($CHCl_3$) 1799 $cm^{-1}$ ($\beta$-lactam C = O); nmr (DMSO-$d_6$) $\delta$3.34 (m, 2, $CH_2Br$), 3.76 (s, 2, side chain $CH_2$), 3.8—4.4 (m), 5.20 (d, 1, J = 5.0 Hz, $C_6$—H) and 5.86 ppm (q, 1, J = 5.0 and 9.0 Hz, $C_7$—H).

PREPARATION 6

Benzhydryl 7-(2-thienylacetamido)-3-(2-iodoethoxycarbonyl)-3-cephem4-carboxylate, 1-oxide To a cooled (ice bath 10 minutes), stirred solution of benzhydryl 7-(2-thieylacetamido)-3-(2-iodoethoxycarbonyl)-2-cepham-4-carboxylate (980 mg., 1.42 mmol.) in 70 ml. chloroform was added dropwise a solution of 85% m-chloroperbenzoic acid (0.319 g., 1.56 mmol.) in 5 ml. of chloroform. The mixture was allowed to stir overnight (11 hours) warming slowing to room temperature. The reaction mixture was washed successively with aqueous sodium bicarbonate (3X), water, and brine, dried over $Na_2SO_4$, and evaporated in vacuo to dryness. Chromatography on 5 g. of silica gel using a toluene-ethyl acetate gradient provided 0.219 g. of the starting material and 0.314 g. of benzhydryl 7-(2-thienylacetamido)-3-(2-iodoethoxycarbonyl)-3-cephem-4-carboxylate, 1-oxide (42% yield, corrected): nmr (DMSO-$d_6$) $\delta 3.03$ (m, $CH_2I$), 3.8–4.3 (m, amide side chain $CH_2$, —$OCH_2$—, and $C_2$—H), 5.05 (d, J = 4.0 Hz, $C_6$—H) and 6.04 (q, 1, J = 4.0 and 8.0 Hz, $C_7$—H).

PREPARATION 7

Benzhydryl 7-(2-thienylacetamido)-3-(2-iodoethoxycarbonyl)-3-cephem-4-carboxylate To a cooled (ice bath 5 minutes), stirred solution of benzhydryl 7-(2-thienylacetamido)-3-(2-iodoethoxycarbonyl)-3-cephem-4-carboxylate, 1-oxide (0.314 g., 0.445 mmol.) in 20 ml. dimethylformamide was added 0.116 ml. of phosphorous trichloride (1.34 mmol., 3.0 eq.). The ice bath was removed and the solution was stirred at room temperature for 45 minutes. Ethyl acetate was added to the reaction mixture, and the resulting mixture was washed with sodium bicarbonate solution (2X), water and brine and then dried over anhydrous $Na_2SO_4$. Evaporation of the solvent in vacuo provided a product which was subsequently chromatographed on silica using a toluene-ethyl acetate gradient to give benzhydryl 7-(2-thienylacetamido)-3-(2-iodoethoxycarbonyl)-3-cephem-4-carboxylate (0.207 g., 68%): nmr (DMSO-$d_6$) $\delta 3.0$ (t, $CH_2$—I), 3.80 (s, 2, side chain $CH_2$), 3.5–4.2 (m, O—$CH_2$—), 5.25 (d, 1, J = 5.0, $C_6$—H), and 5.80 (q, 1, J = 5.0 and 8.0 Ha, $C_7$—H).

PREPARATION 8

Benzhydryl 7-(2-thienylacetamido)-3-carboxy-2-cephem-4-carboxylate

Benzhydryl 7-(2-thienylacetamido)-3-(2-iodoethoxycarbonyl)-2-cepham-4-carboxylate (2.79 g., 4.05 mmol.) was dissolved in a mixture of 8 ml. glacial acetic acid and 48 ml. dimethylformamide and 0° and was reacted with 2.79 g. zinc dust (10.5 eq.) for 1.5 hours. The reaction mixture was diluted with ethyl acetate and filtered through a celite filter. The filtrate was washed successively with sodium bicarbonate solution (3X), water, 1N.HCl, and brine and then dried ($Na_2SO_4$). Evaporation to dryness in vacuo gave 1.92 (89%) of benzhydryl 7-(2-thienylacetamido)-3-carboxy-2-cephem-4-carboxylate: nmr (CDCl$_3$) $\delta 3.84$ (s, side chain $CH_2$), 4.99 (d, 1, J = 4.0 Hz, $C_6$—H), 5.45 (m, $C_4$—H and $C_7$—H) and 7.80 (s, $C_2$—H).

PREPARATION 9

Benzhydryl 7-(2-thienylacetamido)-3-ethylcarbonyldioxycarbonyl-2-cephem-4-carboxylate To a cooled (−10° C.), stirred solution of benzhydryl 7-(2-thienylacetamido)-3-carboxy-2-cephem-4-carboxylate (0.267 g., 0.5 mmol.) in 20 ml. methylene chloride under argon was added 0.051 g. triethylamine (0.5 mmol.). After stirring for several minutes at −10° C., the mixture was cooled to −20 °and 0.162 g., (1.5 mmol.) ethyl chloroformate was added. The reaction mixture was allowed to stir at −20° for 30 minutes, and then allowed to warm to 0°. Cold ethyl acetate was added, and the resultant solution was washed successively with cold water, cold 1N.HCl, and cold brine and then dried ($Na_2SO_4$). Evaporation in vacuo to dryness gave 283 mg. (93.5%) of the mixed anhydride as a colorless froth. ir (CHCl$_3$) 1798 cm$^{-1}$ ($\beta$-lactam C = O); nmr (CDCl$_3$) $\delta 1.34$ (t, 3, J = 7.0 Hz, $CH_2CH_3$), 3.80 (s, 1, side chain $CH_2$), 4.30 (q, 2, J = 7.0 Hz, $CH_2CH_3$), 5.02 (d, 1, J = 4.0 Hz, $C_6$—H), 5.40 (q, 1, J=4.0 and 8.0 Hz, $C_7$—H), 5.55 (s, 1, $C_4$—H), and 4.72 (s, 1, $C_2$—H).

PREPARATION 10

Benzhydryl 7-(2-thienylacetamido)-3-azidocarbonyl-2-cephem-4-carboxylate

To a stirred solution of benzhydryl 7-(2-thienylacetamido)-3-ethylcarbonyldioxycarbonyl-2-cephem-4-carboxylate (0.283 g., 0.468 mmol.) in 20 ml. of tetrahydrofuran at room temperature was added 0.12 g. sodium azide (1.85 mmol.). The mixture was stirred at room temperature for 10 minutes and was then transferred to a separating funnel with the aid of ethyl acetate. The solution was washed with water and brine and subsequently dried ($Na_2SO_4$). Evaporation to dryness gave 265 mg. of the acyl azide as a brown froth: ir (CHCl$_3$) 2143

and 1785 cm$^{-1}$ ($\beta$-lactam C = O); and nmr (CDCl$_3$) $\delta 3.77$ (s, 2, side chain $CH_2$), 4.95 (d, 1, J = 4.0 Hz, $C_6$—H), 5.35 (q, 1, J = 4.0 and 8.0 Hz, $C_7$—H), 5.49 (s, 1, $C_4$—H), and 7.72 (s, 1, $C_2$—H).

PREPARATION 11

Benzhydryl 7-amino-3-(2-bromoethoxycarbonyl)-3-cephem-4-carboxylate

Phosphorous pentachloride (0.186 g., 0.9 mmol.) was added to a stirred slurry of benzhydryl 7-(2-thienylacetamido)-3-(2-bromoethoxycarbonyl)-3-cephem-4-carboxylate (0.500 g., 0.78 mmol.) and pyridine (0.078 ml., 0.962 mmol.) and 9 ml. of methylene chloride. After stirring for two hours and ten minutes at room temperature, the reaction mixture was cooled briefly in a dry ice-acetone bath, and isobutanol (0.39 ml., 4.20 mmol.) was added. The mixture was allowed to stir at ambient temperature for one hour. Addition of n-hexane resulted in the formation of a gum which was then taken up in a slurry of ethyl acetate and sodium bicarbonate solution. The ethyl acetate layer was separated, washed with sodium bicarbonate solution and brine and dried over sodium sulfate. Evaporation in vacuo to dryness gave 0.302 g. (75%) of benzhydryl 7-amino-3-(2-bromoethoxycarbonyl)-3-cephem-4-carboxylate as a brown froth (single spot on tlc).

PREPARATION 12

7-(2-Thienylacetamido)-7-methoxy-3-acetoxymethyl-2-cephem-4-carboxylic acid

To a cooled (0°), stirred solution of 7.75 g. of 7-(2-thienylacetamido)-7-methoxy-3-acetoxymethyl-3-cephem-4-carboxylic acid [prepared from cephalothin in accordance with procedures described by G. A. Koppel and and R. E. Koehler, J. Amer. Chem. Soc., 95, 2403 (1973)]in 46 ml. of dry pyridine was added 5.02 ml. of acetic anhydride. The reaction mixture was allowed to stir with cooling for 2 hours, after which time the mixture was evaporated in vacuo to near dryness. The residue was dissolved in ethyl acetate, and the resulting solution was extracted 3 times with aqueous sodium bicarbonate. The aqueous extracts were combined, layered with ethyl acetate, and acidified with cold 1N.HCl. The organic layer was separated, washed with brine and dried over anhydrous sodium sulfate. Evaporation in vacuo to dryness provided 5.29 g. (68.2 percent) of the title product as a browh froth. Thin layer chromatography of the methyl ester derived from diazomethane exhibited a single spot. For identification purposes a small portion of the product acid was also converted to the corresponding benzhydryl ester using diphenyldiazomethane. Chromatography on a small silica gel column provided pure benzhydryl 7-(2-thienylacetamido)-7-methoxy-3-acetoxymethyl-2-cephem-4-carboxylate: ir (CHCl$_3$) 1780 cm$^{-1}$ ($\beta$-lactam); nmr (CDCl$_3$) $\delta$1.92 (s, 3, OAc), 3.42 (s, 3, OCH$_3$), 3.85 (s, 2, side chain CH$_2$), 4.55 (s, 2, —CH$_2$OAc), 5.01 (m, 1, C$_4$—H), 5.35 (s, 1, C$_6$—H) and 6.35 (m, 6, C$_2$H).

PREPARATION 13

Benzhydryl 7-(2-thienylacetamido)-7-methoxy-3-formyl-2-cephem-4-carboxylate

To a solution of 1.34 g. of 7-(2-thienylacetamido)-7-methoxy-3-acetoxymethyl-2-cephem-4-carboxylic acid in 4 ml. of acetone and 40 ml. of water was added 6.3 ml. of 1N.NaOH. The resulting brown solution was stirred at 45° C. for 15 hours. [Procedure of Cocker et al., J. Chem. Soc. 1142 (1966)]. The mixture was then cooled to room temperature, layered with ethyl acetate and acidified with cold 1N.HCl. The aqueous layer was separated and again extracted with ethyl acetate. The ethyl acetate extracts were combined, washed twice with brine and dried over anhydrous sodium sulfate. Evaporation in vacuo to dryness gave 1.06 g. (87.5 percent) of 7-(2-thienylacetamido)-7-methoxy-3-hydroxymethyl-2-cephem-4-carboxylic acid as a brown froth. The crude acid dissolved in 200 ml. of acetone, was oxidized with 1.15 eq. of chromic acid. The oxidation mixture was allowed to stir at room temperature for five minutes. After five minutes the reaction mixture was evaporated in vacuo to dryness. The residue thereby obtained was dissolved in an ethyl acetate/water slurry. The ethyl acetate layer was separated, washed with brine, dried over anhydrous sodium sulfate, and evaporated in vacuo to dryness to provide 637 mg. of 7-(2-thienylacetamido)-7-methoxy-3-formyl-2-cephem-4-carboxylic acid as a froth. The acid, dissolved in 3 ml. of acetone and 100 ml of ethyl acetate, was reacted with excess diphenyldiazomethane. The mixture was heated to reflux and then allowed to cool to room temperature. Chromatography on 10.0 g. of silica gel using a toluene-ethyl acetate gradient provided 0.509 g. (33.8 percent) of a white froth, the nmr spectrum of which showed it to be a mixture of the benzhydryl ester of the starting 3-acetoxymethyl-2-cephem and the title product, benzhydryl 7-(2-thienylacetamido)-7-methoxy-3-formyl-2-cephem-4carboxylate: nmr (CDCl$_3$) $\delta$3.40 (s, 3, OCH$_3$), 3.84 (s, 2, side chain CH$_2$), 4.60 (s, 2,) 4.88 (C$_2$—H) and 9.20 (s, 1, —CHO).

EXAMPLE 1

Benzhydryl 7-(2-thienylacetamido)-3-isocyanato-2-cephem-4-carboxylate

Benzhydryl 7-(2-thienylacetamido)-3-azidocarbonyl-2-cephem-4-carboxylate was dissolved in toluene and the resulting solution degassed (argon-vacuum) and refluxed gently under argon for 30 minutes. The reaction mixture was cooled to room temperature and evaporated in vacuo to dryness to give the title product in greater than 90% yield:
ir (CDCL$_3$) 2260 (—N=C=O) and 1780 cm$^{-1}$ ($\beta$-lactam C = O); nmr (CDCl$_3$) $\delta$3.84 (s, 2, side chain CH$_2$), 4.99 (s, 1, C$_4$—H), 5.20 (d, 1, J = 4.0 Hz, C$_6$—H), 5.42 (q, 1, J = 4.0 and 8.0 Hz, C$_7$—H) and 5.99 (s, 1, C$_2$—H).

EXAMPLE 2

Benzhydryl 7-(2-thienylacetamido)-3-methoxycarbonylamino-3-cephem-4-carboxylate A solution of 0.376 g. (0.702 mmole) of benzhydryl 7-(2-thienylacetamido)-3-carboxy-2-cephem-4-carboxylate, 0.200 g. (0.729 mmole) of diphenylphosphorylazide and 0.071 g. (0.702 mmole) of triethylamine in 34 ml. of methanol was degassed with argon-vacuum and then refluxed for 36 hours. After this time the reaction mixture was cooled to room temperature and another 0.200 g. of diphenylphosphorylazide and 0.071 g. of triethylamine was added. The resulting mixture was refluxed for eight hours and then cooled to room temperature. The reaction mixture was diluted with ethyl acetate and then washed successively with sodium bicarbonate solution (2X), water, 1N.HCl, and brine and then dried over anhydrous sodium sulfate. The reaction mixture was then evaporated in vacuo to dryness and the resulting product was then chromatographed on silica gel using a toluene-ethyl acetate gradient to give 44 mg. (11.1 percent) of benzhydryl 7-(2-thienylacetamido)-3-methoxycarbonyl-amino-3-cephem-4-carboxylate: ir (CHCl$_3$) 1785 cm$^{-1}$ ($\beta$-lactam C = O); uv max (EtOH) 295 $\mu$ ($\epsilon$=7,750); nmr (CDCl$_3$) $\delta$3.52, 4.35 (AB, 2, J = 16 Hz, C$_2$—H), 3.76 (s, 3, O—CH$_3$), 3.90 (s, 2, side chain CH$_2$), 5.02 (d, 1, J = 4.0 Hz, C$_6$—H), and 5.58 (q, 1, J = 4.0 and 8.0 Hz, C$_7$—H).

EXAMPLE 3

Benzhydryl 7-(2-thienylacetamido)-3-ethoxycarbonylamino-3-cephem-4-carboxylate

A solution of 0.243 g. (0.453 mmole) of benzhydryl 7-(2-thienylacetamido)-3-carboxy-2-cephem-4-carboxylate, 0.137 g. (0.50 mmole) of diphenylphosphorylazide, and 0.05 g. (0.50 mmole) of triethylamine in 35 ml. of 2B ethanol was refluxed 22 hours. The reaction mixture was then cooled to room temperature, diluted with ethyl acetate and washed successively with sodium bicarbonate solution (2X), water, 1N.HCl, and brine and then dried over anhydrous sodium sulfate. The solution was then evaporated in vacuo to dryness and the resulting product was chromatographed on silica gel using a toluene ethyl acetate gradient to provide 0.089 g. (34%) of benzhydryl 7-(2-thienylacetamido)-3-ethoxycarbonylamino-2-cephem-4-carboxylate:

ir (CHCl$_3$) 1783 cm$^{-1}$ ($\beta$-lactam C = O); nmr (CDCl$_3$) $\delta$1.33 (t, 3, J = 7.0 Hz, —CH$_2$CH$_3$), 3.52, 4.41 (AB, 2, J = 16 Hz, C$_2$—H), 3.90 (s, 2, side chain CH$_2$), 4.25 (q, 2, J = 7.0 Hz, —CH$_2$CH$_3$), 5.02 (d, 1, J = 4.0 Hz, C$_6$—H), and 5.50 (q, 1, J = 4.0 and 8.0 Hz, C$_7$—H).

EXAMPLE 4

7-(2-thienylacetamido)-3-ethoxycarbonylamino-3-cephem-4-carboxylic acid

To a cooled (5°), stirred solution of benzhydryl 7-(2-thienylacetamido)-3-ethoxycarbonylamino-3-cephem-4-carboxylate (0.085 g.) in ca. 2 ml. of anisole was added 1 ml. of cold trifluoroacetic acid. The reaction mixture was allowed to stir with cooling for 35 minutes after which time was added approximately 40 ml. of n-heptane. The reaction mixture was then evaporated in vacuo to a low volume and another 20 ml. of n-heptane was added. The white solid which then formed was separated and dissolved in ethyl acetate. The ethyl acetate solution was extracted twice with aqueous sodium bicarbonate. The aqueous extracts were combined, layered with cold ethyl acetate, and then acidified with 1N.HCl. The ethyl acetate layer was separated, washed with brine, dried over anhydrous sodium sulfate, and evaporated in vacuo to dryness to provide 13 mg. of 7-(2-thienylacetamido)-3-ethoxycarbonylamino-3-cephem-4-carboxylic acid as a white solid. A bioautogram of the product exhibited a single spot of antibacterial activity.

EXAMPLE 5

Benzhydryl 7-(2-thienylacetamido)-3-(4-nitrobenzyloxycarbonylamino-3-cephem-4-carboxylate A solution of 0.243 g. (0.453 mmole) of benzhdryl 7-(2-thienylacetamido)-3-carboxy-2-cephem-4-carboxylate, 0.174 g. (1.14 mmole) of 4-nitrobenzyl alcohol, 0.050 g. (0.50 mmole) of triethylamine, and 0.137 g. (50 mmole) of diphenylphosphoryl azide in 20 ml. of benzene was degassed and refluxed for 17 hours. The reaction mixture was then cooled, diluted with ethyl acetate and washed successively with aqueous sodium bicarbonate, water, 1N.HCl, and brine and dried over anhydrous sodium sulfate. The solution was then evaporated in vacuo to dryness, and the resulting product was chromatographed on silica gel using a toluene-ethyl acetate gradient to provide 178 mg. (57.5%) of benzhydryl 7-(2-thienylacetamido)-3-(4-nitrobenzyloxycarbonylamino)-3-cephem-4-carboxylate:

ir (CHCl$_3$) 1785 cm$^{-1}$ ($\beta$-lactam C = O); nmr (CDCl$_3$) $\delta$3.42, 4.16 (AB, 2, J = 16 Hz, C$_2$—H), 3.70 (s, 2, side chain CH$_2$), 4.67 (d, 1, J = 4Hz, C$_6$-H), 5.05 (s, 2, nitrobenzyl CH$_2$), and 5.32 (q, 1, J = 4.0 and 8.0 Hz, C$_7$—H).

EXAMPLE 6

7-(2-thienylacetamido)-3-(4-nitrobenzyloxycarbonylamino)-3-cephem-4-carboxylic acid To a stirred, cooled (5°) solution of 0.339 g. of benzhydryl 7-(2-thienylacetamido)-3-(4-nitrobenzyloxycarbonylamino)-3-cephem-4-carboxylate in 1 ml. of anisole was added 1 ml. of cold trifluoroacetic acid. The reaction mixture was allowed to stir at 5° for 40 minutes after which time was added 30 ml. of n-heptane. The solution was evaporated in vacuo to a low volume and an additional 20 ml. of n-heptane was added. The mixture was stirred with cooling for 5 minutes and thereafter the liquid was decanted off the solid which had formed. The solid was dissolved in ethyl acetate, and the resulting solution was extracted twice with aqueous sodium bicarbonate solution. A precipitate which formed during the extracted was filtered off and dissolved in a slurry of ethyl acetate and 1 N.HCl. The ethyl acetate layer was separated, washed with brine, and dried over anhydrous sodium sulfate. Evaporation of the dried ethyl acetate solution in vacuo to dryness provided 178 mg. (43.4%) of 7-(2-thienylacetamido)-3-(4-nitrobenzyloxycarbonylamino)-3-cephem-4-carboxylic acid as a white solid. The product crystallized from a methylene chloride-acetone/hexane mixture to give 0.11 g. of white platelets (m.p. 149°–150°).

Anal. Calcd. for C$_{21}$H$_{18}$N$_4$O$_8$S$_2$: C, 48.64; H, 3.50; N, 10.81; Found: C, 48.43; H, 3.28; N, 10.55.

EXAMPLE 7

Benzhydryl 7-(2-thienylacetamido)-3-amino-3-cephem-4-carboxylate

A solution of 0.178 g. (0.26 mmole) of benzhydryl 7-(2-thienylacetamido)-3-(4-nitrobenzyloxycarbonylamino)-3-cephem-4-carboxylate in 3 ml. of methylene chloride was combined with 70 ml. of methanol and 0.178 g. of 5 percent palladium on carbon (prereduced with hydrogen at 50 psi for 15 minutes) in 30 ml. of 3A ethanol. The alcoholic mixture was reduced with hydrogen at 50 psi for 3.5 hours. The catalyst was filtered and washed with hot 3A ethanol. The filtrate and washings were combined and evaporated in vacuo to dryness. A methylene chloride solution of the residue thereby obtained was filtered through a celite filter pad. Evaporation in vacuo to dryness provided 128 mg. (97.8 percent) of the title product as a yellow froth: ir (CHCl$_3$) 1720 cm$^{-1}$ ($\beta$-lactam); nmr (CDCl$_3$) $\delta$3.7 (ABq, C$_2$—H), 3.92 (s, 1, side chain CH$_2$), 5.01 (d, 1, J=4.0 Hz, C$_6$—$_H$), 5.32 (q, 1, J = 4.0 Hz, and 8.0 Hz, C$_7$—H), and 6.3 (NH).

EXAMPLE 8

7-(2-Thienylacetamido)-3-amino-3-cephem-4-carboxylic acid

Employing 7-(2-thienylacetamido-3-(4-nitrobenzyloxycarbonylamino)-3-cephem-4-carboxylic acid (Example 6) as starting material, the 4-nitrobenzyloxycarbonylamino group was cleaved reductively in accordance with the procedure described in Example 7. The product exhibited antimicrobial activity in a disc assay at 1 mg/ml.

EXAMPLE 9

Benzhydryl 7-(2-thienylacetamido)-3-(phenylthio)carbonylamino-3-cephem-4-carboxylate A solution of 0.232 g. of benzhydryl 7-(2-thienylacetamido)-3-azidocarbonyl-2-cephem-4-carboxylate in 50 ml. of dry toluene ws refluxed under argon for 30 minutes. After cooling the reaction mixture to room temperature, 0.425 ml. (4.14 mmole) of thiophenol was added, and the resulting mixture was allowed to stir at room temperature for 1 hour. The reaction mixture was then evaporated in vacuo to dryness, and the product thereby obtained was chromatographed on a silica gel column using a toluene-ethyl acetate gradient to provide 90 mg. (34%) of benzhydryl 7-(2-thienylacetamido)-3-(phenylthio)carbonylamino-2-cephem-4-carboxylate:
ir ($CDCl_3$) 1780 $cm^{-1}$ ($\beta$-lactam C = O); nmr ($CDCl_3$) $\delta$3.77 (s, 2, side chain $CH_2$), 5.10 (d, 1, J = 4.0 Hz, $C_6$—H), 5.29 (s, 1, $C_4$—H), and 5.57 (q, 1, J = 4.0 and 8.0 Hz, $C_7$—H).

Five drops of triethylamine was added to a solution of 90 mg. of the above prepared 2-cephem thiocarbamate in 30 ml. of toluene; the resulting solution was stirred at room temperature for 20 minutes. The reaction mixture was diluted with ethyl acetate, subsequently washed with 1N.HCl and brine, and then dried over anhydrous sodium sulfate. Evaporation of the dried solution to dryness in vacuo provided 68 mg. (25.5%) of benzhydryl 7-(2-thienylacetamido)-3-(phenylthio)-carbonylamino-3-cephem-4-carboxylate:
ir ($CHCl_3$) 1781 $cm^{-1}$ ($\beta$-lactam C = O); nmr ($CDCl_3$) $\delta$3.60, 4.20 (AB, 2, J = 16 Hz, $C_2$—H), 3.79 (s, 2, side chain $CH_2$), 4.92 (d, 1, J = 4.0 Hz, $C_6$—H), and 5.56 (q, 1, J = 4.0 and 8.0 Hz $C_7$—H).

EXAMPLE 10

7-(2-thienylacetamido)-3-(phenylthio)carbonylamino-3-cephem-4-carboxylic acid

To a cooled (5°) stirred solution of 68 mg. of benzhydryl 7-(2-thienylacetamido)-3-(phenylthio)carbonylamino-3-cephem-4-carboxylate in 1 ml. of anisole was added 1 ml. of cold trifluoroacetic acid. The reaction mixture was allowed to stir with cooling for 20 minutes after which time was added approximately 30 ml. of n-heptane. The resulting solution was evaporated in vacuo to a low volume. An additional 5 ml. of n-heptane was added, and the resulting solution was stirred in an ice bath for 5 minutes. The solution was filtered, and the precipitate thereby obtained was dissolved in acetone. The acetone solution was then filtered, and the filtrate evaporated in vacuo to dryness. The solution obtained by dissolving the residue in ethyl acetate was extracted twice with aqueous sodium bicarbonate solution. The aqueous extracts were combined, layered with cold ethyl acetate and acidified with cold 1N.HCl. The ethyl acetate layer was separated, washed with brine, dried over anhydrous sodium sulfate, and evaporated in vacuo to dryness to provide 33 mg. of the title product as a white solid.

EXAMPLE 11

Benzhydryl 7-(2-thienylacetamido)-3-(N,N-dimethylureido)-3-cephem-4-carboxylate

A solution of benzhydryl 7-(2-thienylacetamido)-3-azidocarbonyl-2-cephem-4-carboxylate (0.254 g., 0.453 mmole) in 30 ml. of dry toluene was degassed (vacuum-argon) and refluxed under an argon atmosphere for 30 minutes. The reaction mixture was cooled to 0°, and 7 drops of dimethylamine was added. The reaction mixture was stirred under an argon atmosphere in an ice bath for approximately 1 hour. The reaction mixture was then evaporated in vacuo to dryness to give a product which was chromatographed on a silica gel column using a toluene-ethyl acetate gradient to provide 0.171 g. (65.2%) of the title compound:
ir ($CHCl_3$) 1778 $cm^{-1}$ ($\alpha$-lactam C = 0); nmr $CDCl_3$) $\delta$2.97 (s, 6, dimethyl), 3.35, 4.70 (ABq, 2, J = 16 Hz, $C_2$-H), 2.85 (s, 2, side chain $CH_2$), 5.05 (d, 1, J = 4 Hz, $C_6$-H), 5.50 (q, 1, J = 4.0 and 8.0 Hz, $C_7$-H).

EXAMPLE 12

7-2-thienylacetamido)-3-(N, N-dimethylureido)-3-cephem-4-carboxylic acid

To a cooled (5°) stirred solution of benzyhydryl 7-(2-thienylacetamido)-3-(N,N-dimethylureido-3-cephem-4-carboxylate (0.171 g., 0.297 mmole) in 1ml. of anisole was added 1 ml. of cold trifluoroacetic acid. The reaction mixture was allowed to stir with cooling for 20 minutes after which time was added 30 ml. of n-heptane. The resulting solution was evaporated in vacuo to a low volume. An additional 20 ml. of n-heptane was added to the residue; the resulting solution was stirred in an ice bath for 5 minutes. The solvent was decanted off the white solid which had precipitated. This solid was dissolved in acetone, the resulting solution filtered, and the filtrate evaporated in vacuo to dryness. The product thereby obtained was dissolved in ethyl acetate, and the resulting solution was extracted twice with aqueous sodium bicarbonate solution. The aqueous extracts were combined and layered with cold ethyl acetate, and the resulting slurry was acidified with 1N.HCl. The ethyl acetate layer was separated, washed with brine, dried over anhydrous sodium sulfate, and evaporated in vacuo to dryness to provide 96 mg. of the title product as a white amorphous solid.

EXAMPLE 13

Benzyhydryl 7-(2-thienylacetamido)-3-di(methoxycarbonyl)-acetamido-3-cephem-4 -carboxylate To a cooled (−10°) stirred solution of 69 mg. (0.525 mmole) of dimethylmalonate in 10 ml. dry tetrahydrofuran was added 25 mg. (0.525 mmole) of 50% sodium hydride. The reaction mixture was allowed to stir at 0° for 10 minutes under an argon atmosphere after which time the reaction mixture was cooled to −20° and a solution of 0.232 g. (0.436 mmole) of benzhydryl 7-(2-thienylacetamido)-3-isocyanato-2-cephem-4-carboxylate in 8 ml. of dry tetrahydrofuran was added dropwise. The reaction mixture was allowed to stir at −20° for ten minutes and then at 0° for 15 minutes. After the mixture was then cooled to −5°, 5 ml. of 1N.HCl was added dropwise. The reaction mixture was diluted with cold ethyl acetate, and the resulting solution was washed successively with 1N.HCl, water, and brine and then dried over anhydrous sodium sulfate. The product obtained by evaporating the ethyl acetate solution in vacuo to dryness was chromatographed on a silica gel column using a toluene-ethyl acetate gradient to provide 84 mg. (29%) of the title product: ir $(CHCl_3)$ 1785 $cm^{-1}$ ($\beta$-lactam C = 0); nmr $(CDCl_3)$ $\delta$3.70, 4.25 (AB, 2, J = 16 Hz, $C_2$—H), 3.8 (m, 8, side chain $CH_2$ and $(COOCH_3)_2$), 4.45 (s, 1, $CH(COOCH_3)_2$), 4.93 (d, 1, J = 4.0 Hz, $C_6H$), and 5.67 (q, 1, J = 4.0 and 8.0 Hz, $C_7$—H).

EXAMPLE 14

7-(2-theinylacetamido)-3-di(methoxycarbonyl)acetamido-3-cephem-4-carboxylic acid To a cooled (5°), stirred slurry of 84 mg. of benzhydryl 7-(2-thienylacetamido)-3-di(methoxycarbonyl)acetamido-3-cephem-4-carboxylate in 1 ml. of anisole was added 1 ml. of cold trifluoroacetic acid. The reaction mixture was allowed to stir at 5° for 10 minutes after which time was added approximately 30 ml. of n-heptane. The resulting solution was evaporated in vacuo to a low volume. An additional 30 ml. of n-heptane was added and the resulting solution was stirred in an ice bath for 5 minutes during which time a solid precipitated. The solid was separated by filtration, dissolved in acetone, the resulting solution was filtered, and the filtrate thereby obtained was evaporated in vacuo to dryness. The residue was dissolved in ethyl acetate, and the resulting solution was extracted twice with cold aqueous sodium bicarbonate. The aqueous bicarbonate extracts were combined, layered with cold ethyl acetate, and acidified with cold 1N.HCl. The ethyl acetate layer was then separted, washed with brine, dried over anhydrous sodium sulfate and evaporated in vacuo to dryness to provide 39 mg. (62%) of the title compound.

I claim:
1. A compound of the formula

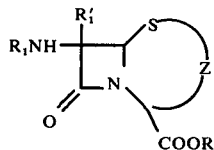

wherein Z is a group of the formula

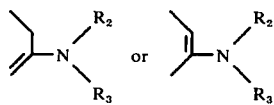

wherein $R_2$ and $R_3$ are each hydrogen or taken together form the group =C=O, wherein $R_2$ taken singly is hydrogen and $R_3$ taken singly is
a. a group of the formula

wherein $R_4$ is $C_1$–$C_6$ alkyl, $C_3$–$C_6$ alkenyl, $C_1$–$C_6$ haloalkyl, 2,2,2-trihaloethyl, methoxybenzyl, nitrobenzyl, benzyl or phenyl; or b. a group of the formula

wherein $R_5$ is $C_1$–$C_6$ alkyl, phenyl, or benzyl; or
c. a group of the formula

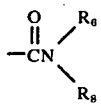

wherein $R_6$ is hydrogen, $C_1$–$C_6$ alkyl, benzyl, phenyl, or tolyl and $R_8$ is hydrogen, $C_1$–$C_6$ alkyl or benzyl; or wherein $R_6$ and $R_8$ and the nitrogen atom to which they are bonded taken together form a 5 or 6 membered heterocyclic ring selected from the group consisting of piperidine, morpholine, and pyrrolidine; or
d. a group of the formula

wherein $R_7$ is $C_1$–$C_6$ alkyl, di($C_1$–$C_3{}'$ alkoxycarbonyl)methyl, benzyl or phenyl; and
wherein R is hydrogen or a carboxylic acid protecting ester forming group; $R_1{}'$ is hydrogen; and wherein $R_1$ is an acyl group of the formula

wherein R' is
a. $C_1$–$C_7$ alkyl, $C_3$–$C_7$ alkenyl, cyanomethyl, halomethyl, 4-amino-4-carboxybutyl, 4-protected amino-4-protected carboxybutyl; or
b. $C_1$–$C_6$ alkoxy, benzyloxy, 4-nitrobenzyloxy or 4-methyoxybenzyloxy; or
c. the group —R" wherein R" is 1,4-cyclohexadienyl, phenyl, or substituted phenyl wherein the substituents are 1–3 halogens, hydroxy, nitro, cyano, trifluoromethyl, $C_1$–$C_4$ alkyl, $C_1$–$C_4$ alkoxy, carboxy, caraboxymethyl, hydroxymethyl, aminomethyl, or protected aminomethyl; or
d. an arylalkyl group of the formula

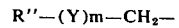

wherein R" is as defined above,
X is O or S, and
m is 0 or 1; or
e. a substituted arylalkyl group of the formula

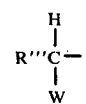

wherein R'" is R" as defined above, 2-thienyl, or 3-thienyl; W is hydroxy or protected hydroxy, carboxy or protected carboxy, amino, protected amino; or f. a heteroarylmethyl group of the formula

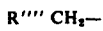

wherein R'''' is 2-theinyl, 3-theinyl, 2-furyl, 3-furyl, 2thiazolyl, 5-tetrazolyl or 1-tetrazolyl;
and when R is hydrogen, the pharmaceutically acceptable non-toxic salts of the acids represented thereby; with the limitations that when $R_3$ is

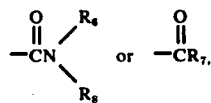

, Z can only be

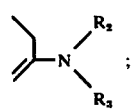

and when the group

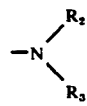

is —N=C=O, R cannot be hydrogen.

2. The compound of claim 1 wherein R is hydrogen, diphenylmethyl, 4-methoxybenzyl, dimethylallyl, or tert-butyl, and when R is hydrogen, the pharmaceutically acceptable nontoxic salts of the acid represented thereby.

3. The compound of claim 2 wherein Z is a group of the formula

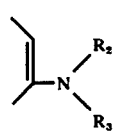

4. The compound of claim 3 wherein $R_2$ and R taken together form the group =C=O.

5. The compound of claim 4 wherein R' is 2-thienylmethyl.

6. The compound of claim 3 wherein $R_2$ taken singly is hydrogen and $R_3$ taken singly is a group of the formula

7. The compound of claim 3 wherein $R_2$ taken singly is hydrogen and $R_3$ taken singly is a group of the formula

8. The compound of claim 2 wherein Z is a group of the formula

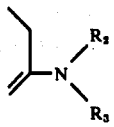

9. The compound of claim 8 wherein $R_2$ and $R_3$ taken together form the group =C=O.

10. The compound of claim 9 wherein R' is 2-thienylmethyl.

11. The compound of claim 8 wherein $R_2$ and $R_3$ are each hydrogen.

12. The compound of claim 8 wherein R is hydrogen.

13. The compound of claim 12 wherein $R_2$ taken singly is hydrogen and $R_3$ taken singly is a group of the formula

14. The compound of claim 12 wherein $R_2$ taken singly is hydrogen and $R_3$ taken singly is a group of the formula

15. The compound of claim 12 wherein $R_2$ taken singly is hydrogen and $R_3$ taken singly is a group of the formula

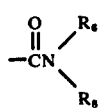

16. The compound of claim 12 wherein $R_2$ taken singly is hydrogen and $R_3$ singly is a group of the formula

17. The compound of claim 12 wherein R' is an arylalkyl group of the formula R''—(Y)m—CH$_2$—.

18. The compound of claim 12 wherein R' is a substituted arylalkyl group of the formula

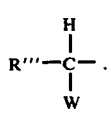

19. The compound of claim 18 wherein W is hydroxy or formyloxy and R''' is phenyl.

20. The compound of claim 19 said compound being 7-(2-formyloxy-2-phenylacetamido)-3-ethoxycarbonylamino-3-cephem-4-carboxylic acid.

21. The compound of claim 12 wherein R' is 2-thienylmethyl.

22. The compound of claim 21 wherein $R_2$ taken singly is hydrogen and $R_3$ singly is a group of the formula

$-COR_4$.

23. The compound of claim 22, wherein $R_4$ is methyl, ethyl or 4-nitrobenzyl.

24. The compound of claim 21 wherein $R_2$ taken singly is hydrogen and $R_3$ taken singly is a group of the formula

$-CSR_5$.

25. The compound of claim 24 wherein $R_5$ is phenyl.

26. The compound of claim 21 wherein $R_2$ taken singly is hydrogen and $R_3$ taken singly is a group of the formula

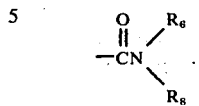

27. The compound of claim 26 wherein $R_6$ and $R_8$ are each methyl.

28. The compound of claim 21 wherein $R_2$ taken singly is hydrogen and $R_3$ taken singly is a group of the formula

$-CR_7$.

29. The compound of claim 28 wherein $R_7$ is di(methoxycarbonyl)methyl.

30. The compound of claim 28 wherein $R_7$ is methyl, ethyl, benzyl or phenyl.

* * * * *